(12) United States Patent
Garcia Diaz et al.

(10) Patent No.: US 11,724,033 B2
(45) Date of Patent: Aug. 15, 2023

(54) METHOD AND APPARATUS FOR DELIVERING DRUGS TO THE SPINE OF A PATIENT, AND/OR FOR DELIVERING OTHER MATERIALS AND/OR DEVICES TO THE SPINE OF A PATIENT

(71) Applicant: Pain Away Solutions, LLC, Merced, CA (US)

(72) Inventors: Gabriel Garcia Diaz, Merced, CA (US); Tov Vestgaarden, Largo, FL (US); Jason Schinis, Largo, FL (US)

(73) Assignee: Pain Away Solutions, LLC, Merced, CA (US)

( * ) Notice: Subject to any disclaimer, the term of this patent is extended or adjusted under 35 U.S.C. 154(b) by 0 days.

(21) Appl. No.: 17/061,022

(22) Filed: Oct. 1, 2020

(65) Prior Publication Data

US 2021/0085872 A1  Mar. 25, 2021

Related U.S. Application Data

(63) Continuation-in-part of application No. 16/380,777, filed on Apr. 10, 2019, now abandoned.

(60) Provisional application No. 62/908,717, filed on Oct. 1, 2019, provisional application No. 62/655,666, filed on Apr. 10, 2018.

(51) Int. Cl.
| | | |
|---|---|---|
| *A61M 5/20* | (2006.01) | |
| *A61M 5/32* | (2006.01) | |
| *A61B 17/34* | (2006.01) | |
| *A61B 17/00* | (2006.01) | |
| *A61B 90/00* | (2016.01) | |

(52) U.S. Cl.
CPC ....... *A61M 5/2033* (2013.01); *A61B 17/3403* (2013.01); *A61M 5/3295* (2013.01); *A61B 2017/0092* (2013.01); *A61B 2090/3966* (2016.02); *A61M 2210/1003* (2013.01)

(58) Field of Classification Search
CPC .................. A61M 5/3295; A61M 5/32; A61M 2210/1003; A61M 5/2033; A61M 5/427; A61B 17/3403; A61B 8/0841; A61B 2017/0092; A61B 2090/3966; A61B 2017/3405; A61B 2017/3407; A61B 2017/3411
See application file for complete search history.

(56) References Cited

U.S. PATENT DOCUMENTS

| | | | |
|---|---|---|---|
| 3,941,127 | A | 3/1976 | Froning |
| 9,387,008 | B2 * | 7/2016 | Sarvestani ......... A61B 17/3403 |
| 2004/0092894 | A1 * | 5/2004 | Hung .................. A61M 5/1408 |
| | | | 604/284 |
| 2012/0265098 | A1 | 10/2012 | McGhie |
| 2013/0085342 | A1 | 4/2013 | Stefanchik et al. |
| 2014/0343500 | A1 * | 11/2014 | Fielder ............... A61B 17/1739 |
| | | | 604/288.01 |

(Continued)

*Primary Examiner* — Katherine H Schwiker
*Assistant Examiner* — Robert F Allen
(74) *Attorney, Agent, or Firm* — Pandiscio & Pandiscio

(57) ABSTRACT

A drug delivery system comprising: a plurality of needles; a needle guide for guiding and holding the plurality of needles during insertion into a patient's spine; a syringe containing a drug which is to be delivered into the patient's spine; a port multiplier comprising an inlet port connectable to the syringe and a plurality of outlet ports; and a plurality of tubes for providing fluid connections between the outlet ports of the port multiplier and the plurality of needles.

42 Claims, 24 Drawing Sheets

(56) References Cited

U.S. PATENT DOCUMENTS

| | | |
|---|---|---|
| 2015/0096562 A1 | 4/2015 | Dunsmore et al. |
| 2016/0038677 A1* | 2/2016 | Kiilerich ............... F16F 1/10 |
| | | 604/211 |
| 2016/0074119 A1 | 3/2016 | Boulis et al. |
| 2016/0213443 A1* | 7/2016 | Lueck ............... A61G 13/101 |
| 2016/0256621 A1 | 9/2016 | Toro et al. |

* cited by examiner

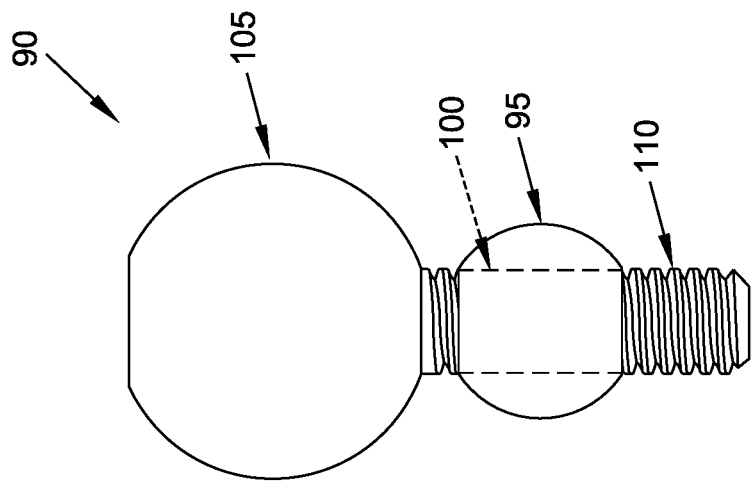
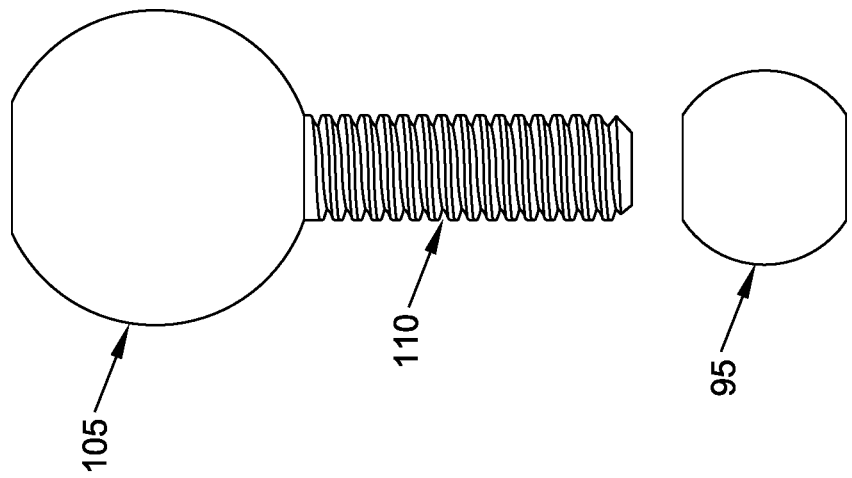

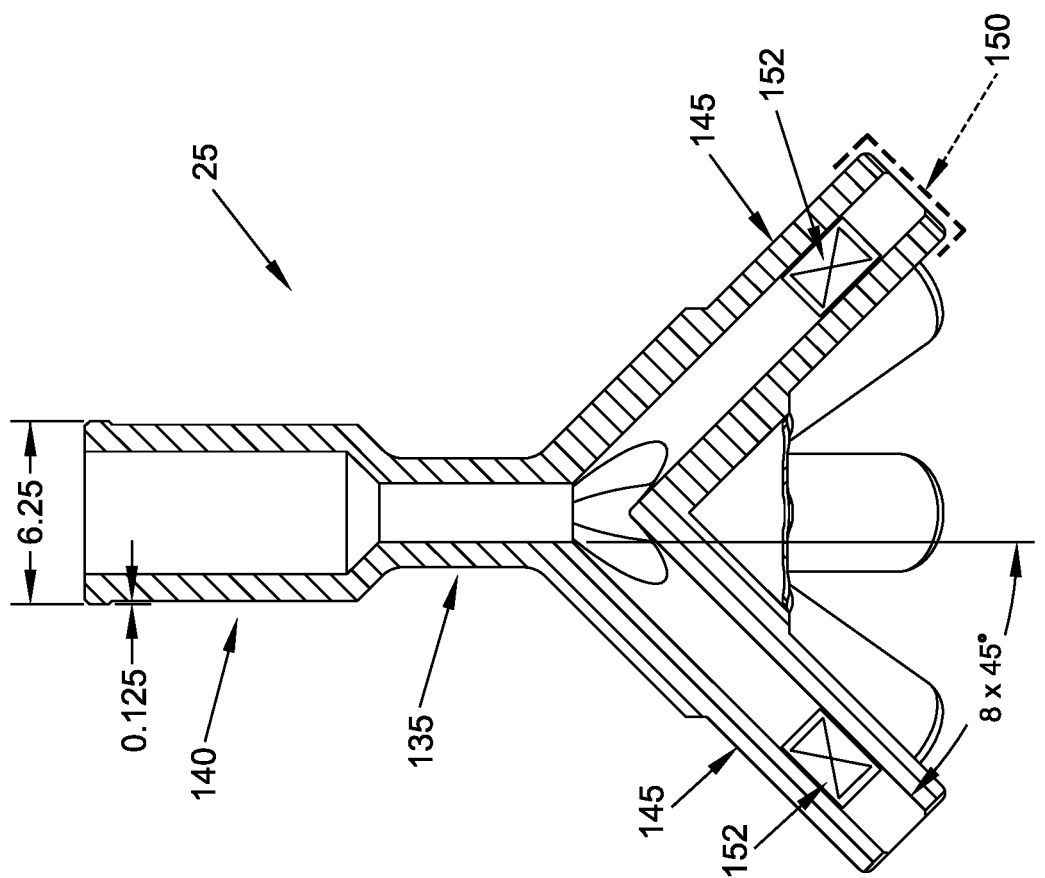

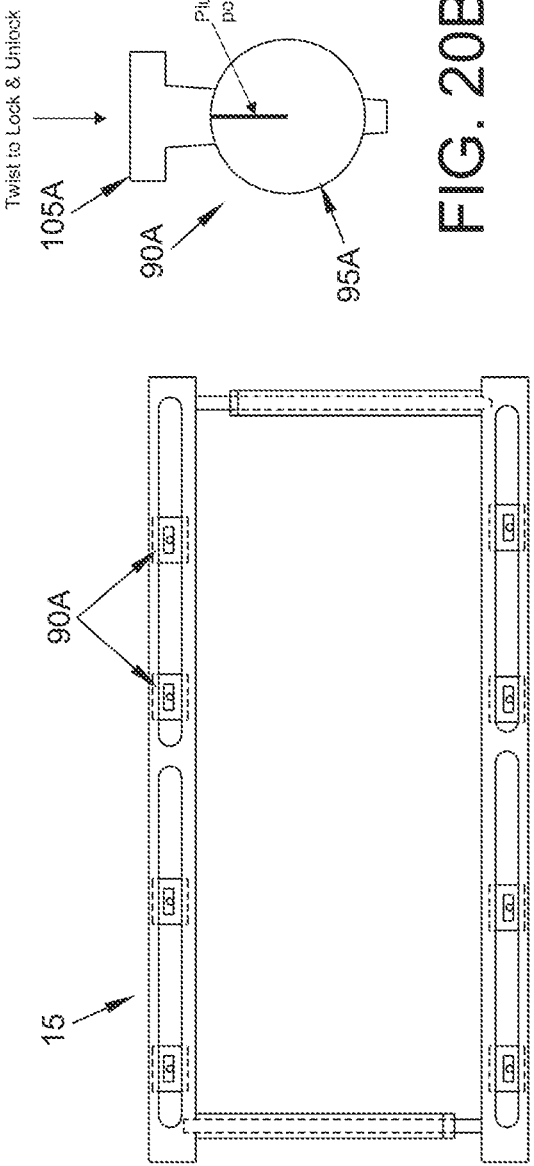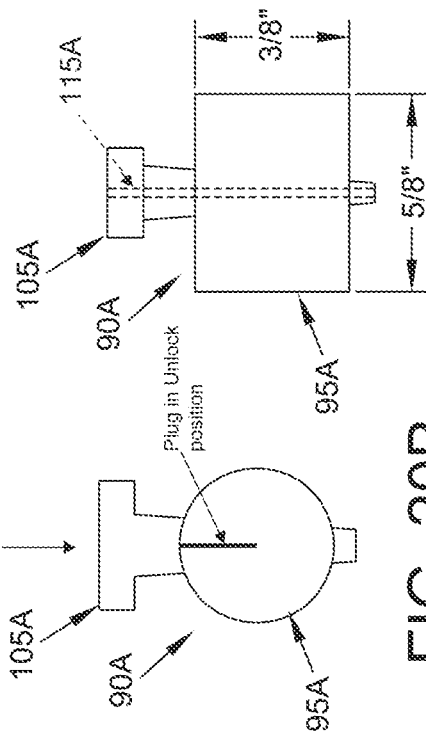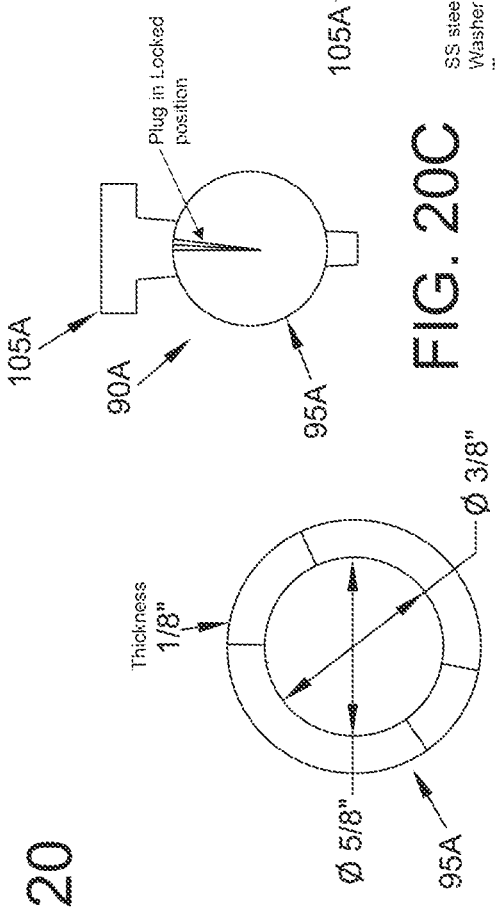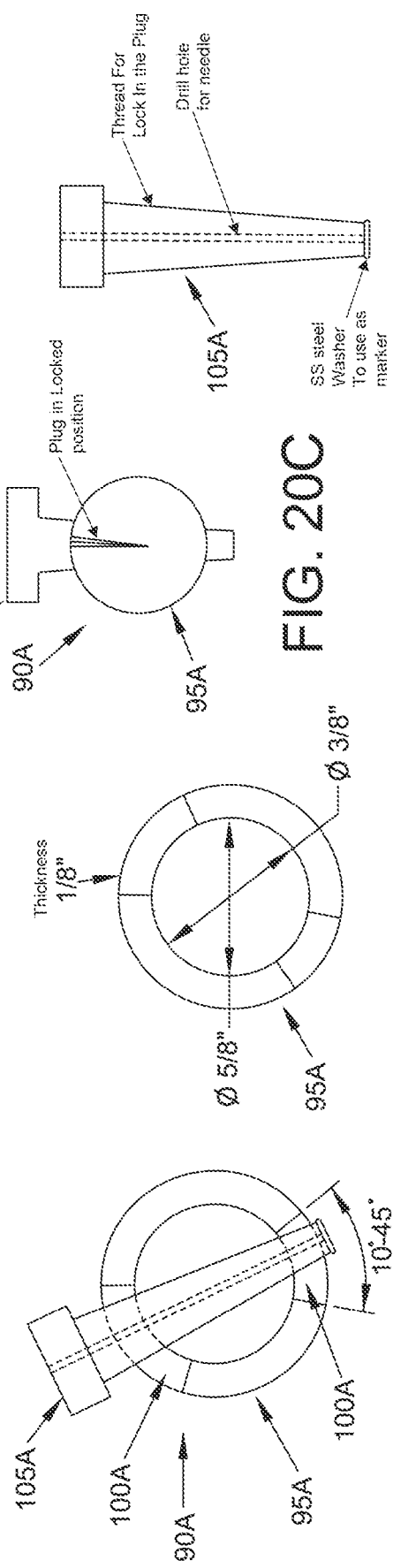

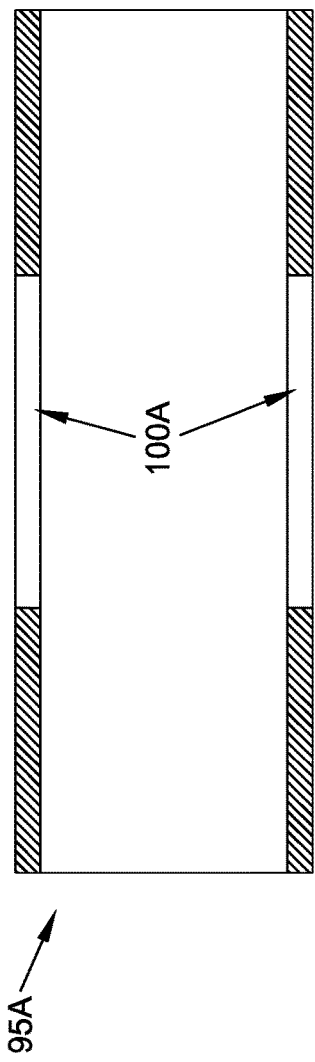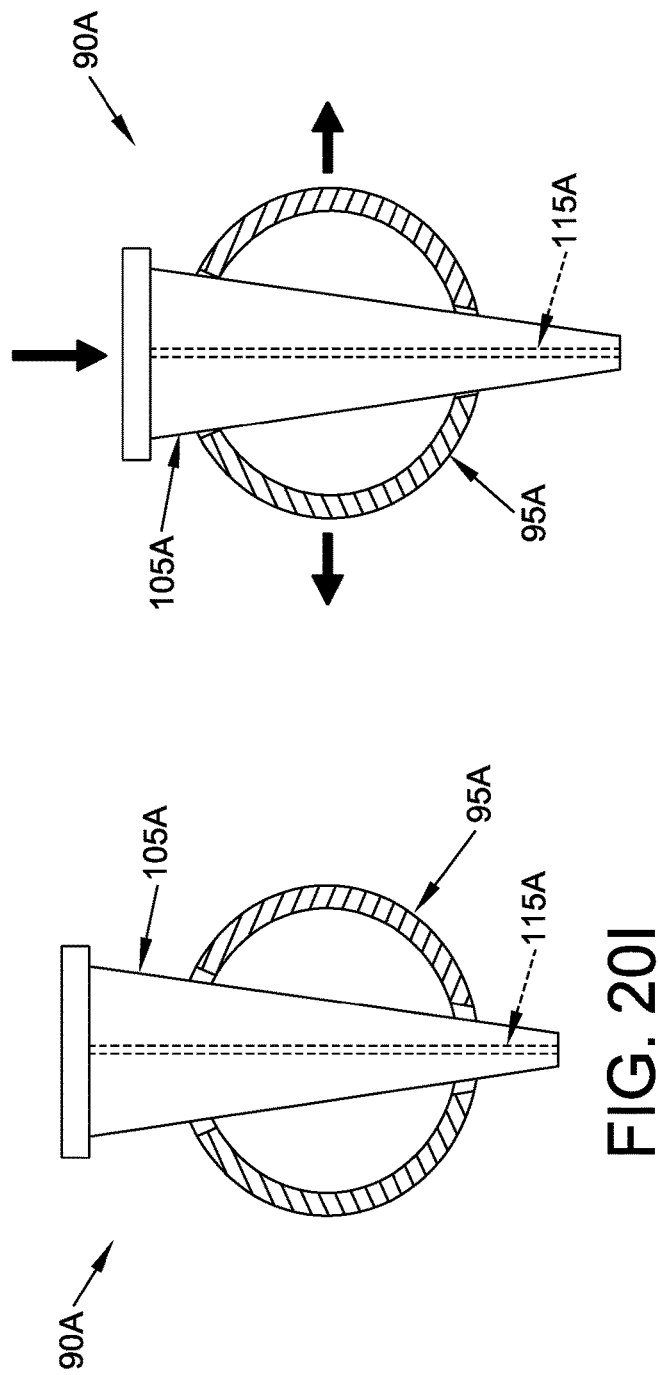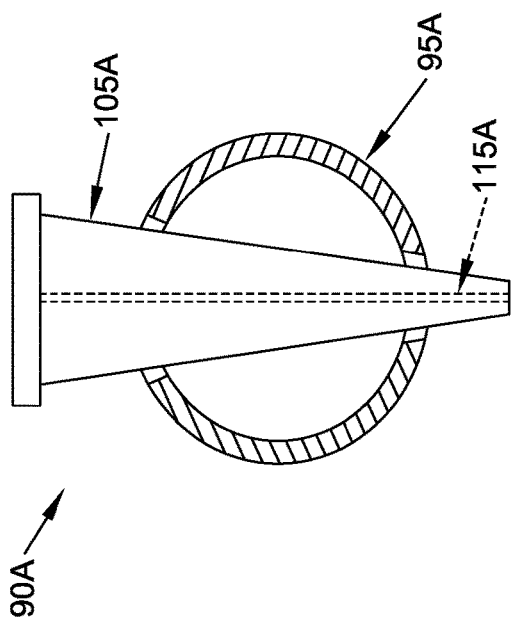

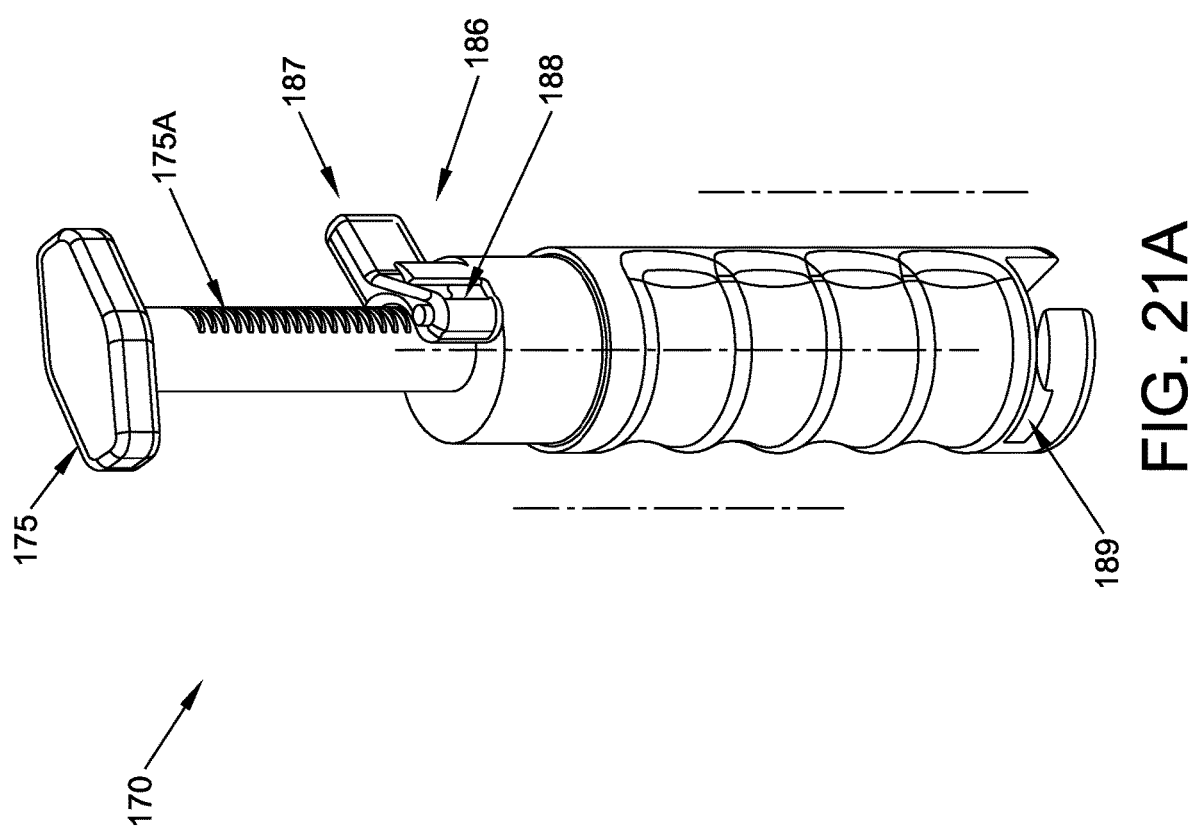

METHOD AND APPARATUS FOR DELIVERING DRUGS TO THE SPINE OF A PATIENT, AND/OR FOR DELIVERING OTHER MATERIALS AND/OR DEVICES TO THE SPINE OF A PATIENT

REFERENCE TO PENDING PRIOR PATENT APPLICATIONS

This patent application:

(1) is a continuation-in-part of pending prior U.S. Non-Provisional patent application Ser. No. 16/380,777, filed Apr. 10, 2019 by Pain Away Solutions, LLC and Gabriel Garcia Diaz for LUMBAR SYRINGE GUIDE ASSEMBLY, which patent application claims benefit of:

(A) prior U.S. Provisional Patent Application Ser. No. 62/655,666, filed Apr. 10, 2018 by Gabriel Garcia Diaz for LUMBAR SYRINGE GUIDE ASSEMBLY; and (2) claims benefit of prior U.S. Provisional Patent Application Ser. No. 62/908,717, filed Oct. 1, 2019 by Pain Away Solutions, LLC and Gabriel Garcia Diaz et al. for METHOD AND APPARATUS FOR DELIVERING DRUGS TO THE SPINE OF A PATIENT, AND/OR FOR DELIVERING OTHER MATERIALS AND/OR DEVICES TO THE SPINE OF A PATIENT.

The three (3) above-identified patent applications are hereby incorporated herein by reference.

FIELD OF THE INVENTION

This invention relates to drug delivery systems in general, and more particularly to drug delivery systems for delivering drugs to the spine of a patient. This invention also relates to delivering other materials and/or devices to the spine of a patient. Among other things, the present invention comprises a system of different components which are intended to be used collectively for the purpose of delivering drugs to the spine of a patient. However, it should also be appreciated that the different components (i.e., devices) of the system may be used independently of one another, or may be used with other devices, or may be used for other purposes, etc., such as utilizing the spring-loaded syringe assist device (see below) for assisting in the delivery of intravenous medications to patients. Also, the needle guide (see below) may be used for pedicle screw placement, with or without the use of navigation software, etc.

BACKGROUND OF THE INVENTION

Physicians frequently need to inject drugs into the spine of a patient, e.g., to treat patients with chronic back pain. In many cases, the spinal injection must be fluoroscope-guided to ensure that the drugs are placed into the correct locations in the patients' anatomy. In many cases, an individual patient may need to have injections in multiple locations within the spine.

Currently, physicians handle one needle at a time, which means that they need to find the correct location for each needle placement prior to insertion of the medication of the syringe into the patient. The need to handle each needle independently leaves room for error, particularly when it comes to the precision of the insertion of the needle into a patient's anatomy. Moreover, because each needle has to be handled separately, this adds time to the procedure and, in some cases, additional radiation exposure to the patient and the healthcare staff involved in the care of the patient.

Therefore, there is a need for a novel drug delivery system which assists a physician in inserting and holding in place multiple needles, while ensuring the accuracy of the insertion angles and locations of the multiple needles, and delivers medication through the multiple needles to a patient.

SUMMARY OF THE INVENTION

The present invention relates to a method and apparatus for delivering drugs to the spine of a patient.

More particularly, the present invention comprises the provision and use of a novel drug delivery system which comprises a plurality of needles; a needle guide for guiding and holding the plurality of needles during insertion into the patient's spine; a syringe containing the drug which is to be delivered into the patient's spine; a port multiplier comprising an inlet port and a plurality of outlet ports; and a plurality of tubes for providing a connection between the outlet ports of the port multiplier and the plurality of needles.

In use, the needle guide is positioned against the skin of the patient adjacent to the spine; the needle guide is used to guide the plurality of needles as they are inserted into the spine and to hold them in position; the port multiplier is connected to the syringe containing the drug which is to be delivered; tubes are used to connect the outlet ports of the port multiplier to the needles; and the syringe is used to eject the drug into the port multiplier, through the tubes and through the needles so as to be injected into the desired locations in the spine of the patient.

The present invention may also be used for delivering other materials (e.g., non-drug fluids including biologics, etc.) and/or devices (e.g., pedicle screws, bone implants, etc.) to the spine of a patient.

In one form of the invention, there is provided a drug delivery system comprising:

a plurality of needles;

a needle guide for guiding and holding the plurality of needles during insertion into a patient's spine;

a syringe containing a drug which is to be delivered into the patient's spine;

a port multiplier comprising an inlet port connectable to the syringe and a plurality of outlet ports; and a plurality of tubes for providing fluid connections between the outlet ports of the port multiplier and the plurality of needles.

In another form of the invention, there is provided a method for delivering drugs, the method comprising:

providing a drug delivery system comprising:

a plurality of needles;

a needle guide for guiding and holding the plurality of needles during insertion into a patient's spine;

a syringe containing a drug which is to be delivered into the patient's spine;

a port multiplier comprising an inlet port connectable to the syringe and a plurality of outlet ports; and a plurality of tubes for providing fluid connections between the outlet ports of the port multiplier and the plurality of needles;

positioning the needle guide against the skin of the patient adjacent to the spine;

using the needle guide to guide the plurality of needles as they are inserted into the spine and hold them in position;

connecting the port multiplier to the syringe containing the drug which is to be delivered;

connecting the tubes to the outlet ports of the port multiplier and to the needles; and using the syringe to eject the drug into the port multiplier, through the tubes and through the needles so as to be injected into the desired locations in the spine of the patient.

In another form of the invention, there is provided a delivery system for delivering a plurality of cannulated devices into the anatomy of a patient, the delivery system comprising:

a plurality of guidewires;

a frame; and a plurality of guidewire supports selectively movably mounted to the frame, wherein each of the guidewire supports is configured to guide and hold a guidewire during insertion into the anatomy of a patient;

wherein the frame comprises two frame supports connected to one another by at least one adjustable arm;

wherein each of the frame supports comprises a frame lumen and a pair of slots communicating with the frame lumen;

wherein each of the guidewire supports comprises:

a body slidably disposed in a frame lumen of a frame support; and a member configured to slidably support a guidewire and to selectively lock the body in a selected position within a frame lumen of a frame support.

In another form of the invention, there is provided a method for delivering a plurality of cannulated devices into the anatomy of a patient, the method comprising:

providing a delivery system comprising:

plurality of guidewires;

a frame; and a plurality of guidewire supports selectively movably mounted to the frame, wherein each of the guidewire supports is configured to guide and hold a guidewire during insertion into the anatomy of a patient;

wherein the frame comprises two frame supports connected to one another by at least one adjustable arm;

wherein each of the frame supports comprises a frame lumen and a pair of slots communicating with the frame lumen;

wherein each of the guidewire supports comprises:

a body slidably disposed in a frame lumen of a frame support; and a member configured to slidably support a guidewire and to selectively lock the body in a selected position within a frame lumen of a frame support;

positioning the frame against the anatomy of the patient;

using the plurality of guidewire supports to guide the plurality of guidewires as they are inserted into the anatomy of the patient;

withdrawing the frame and the plurality of guidewire supports while leaving the plurality of guidewires inserted into the anatomy of the patient; and delivering a plurality of cannulated devices into the anatomy of a patient by passing the cannulated devices over the plurality of guidewires.

In another form of the invention, there is provided a guide for guiding and holding a plurality of objects during insertion into a patient's body, the guide comprising:

a frame; and a plurality of object supports selectively movably mounted to the frame, wherein each of the object supports is configured to guide and hold an object during insertion into the patient's body;

and further wherein each of the object supports is reconfigurable between:

(i) a first configuration wherein the object support is movable at least one of (a) axially along the frame and (b) rotatably relative to the frame; and (ii) a second configuration wherein the object support is fixed relative to the frame.

In another form of the invention, there is provided a syringe assist device for use with a syringe, wherein the syringe comprises (a) a syringe body having a cavity and an output port, and (b) a plunger movably disposed in the cavity for driving the contents of the cavity out of the output port, the syringe assist device comprising:

a housing for mounting to the syringe body;

a driver for engaging the plunger and moving the plunger so as to drive the contents of the cavity out of the output port; and a power unit for moving the driver.

In another form of the invention, there is provided a port multiplier comprising:

a hollow body having an interior;

an input port in fluid communication with the interior of the hollow body, the input port being configured for attachment to a syringe; and a plurality of output ports in fluid communication with the interior of the hollow body, each of the plurality of output ports being configured for attachment to a fluid line.

BRIEF DESCRIPTION OF THE FIGURES

These and other objects and features of the present invention will be more fully disclosed or rendered obvious by the following detailed description of the preferred embodiments of the invention, which is to be considered together with the accompanying drawings wherein like numbers refer to like parts, and further wherein:

FIGS. 1-8, 8A, 9, 10, 10A and 11-19 are schematic views showing one preferred form of the present invention;

FIGS. 20 and 20A-20J are schematic views showing an alternative form of the needle guide;

FIG. 21A is a schematic view showing an alternative form of the spring-loaded syringe assist device of FIG. 21.

DETAILED DESCRIPTION OF THE PREFERRED EMBODIMENTS

Figure 1:
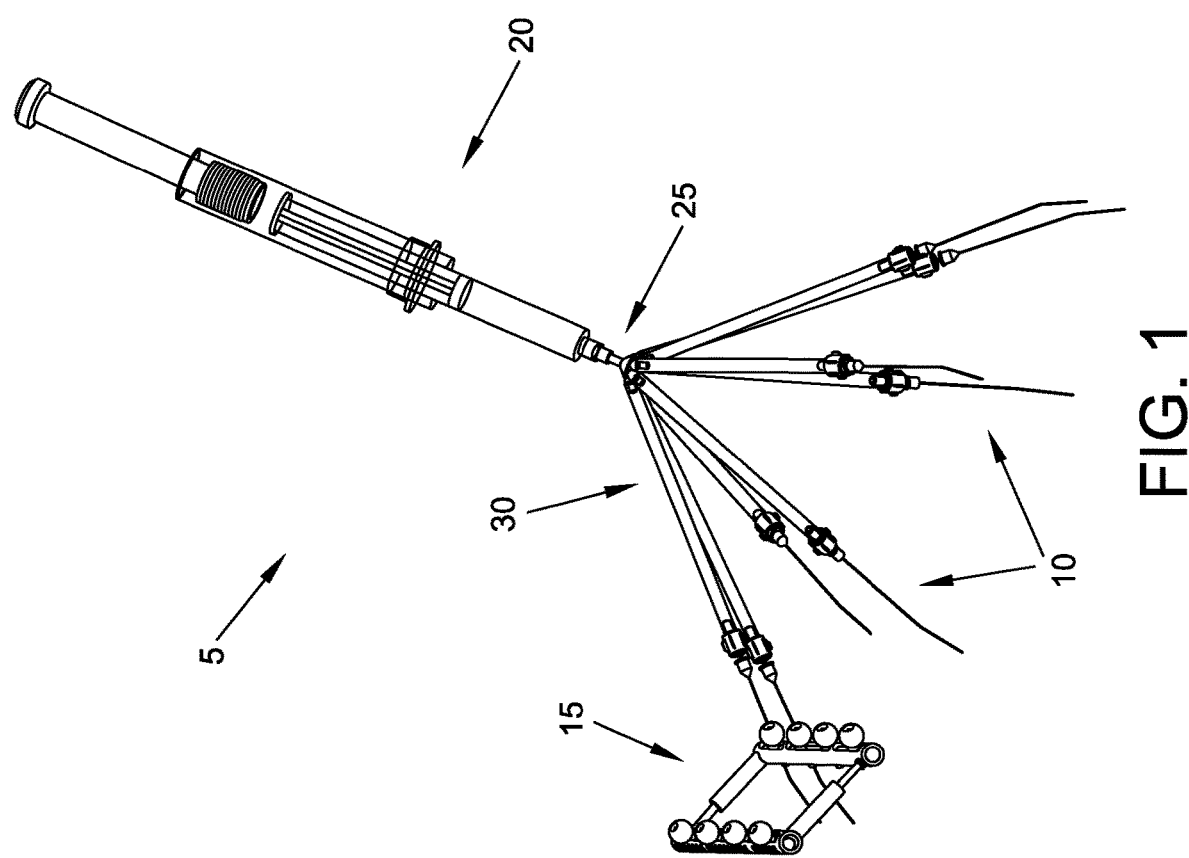
Figure 2:
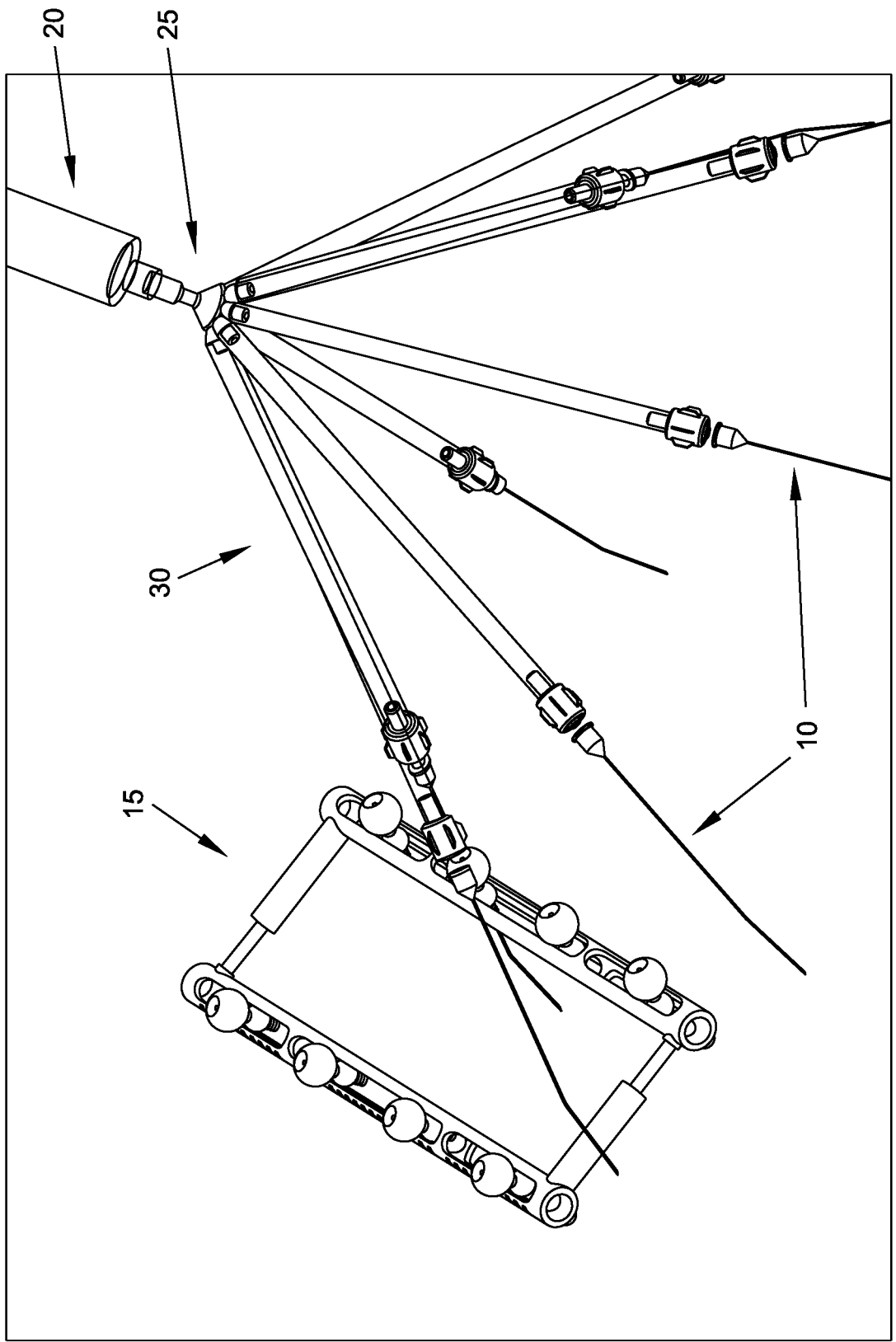
Figure 3:
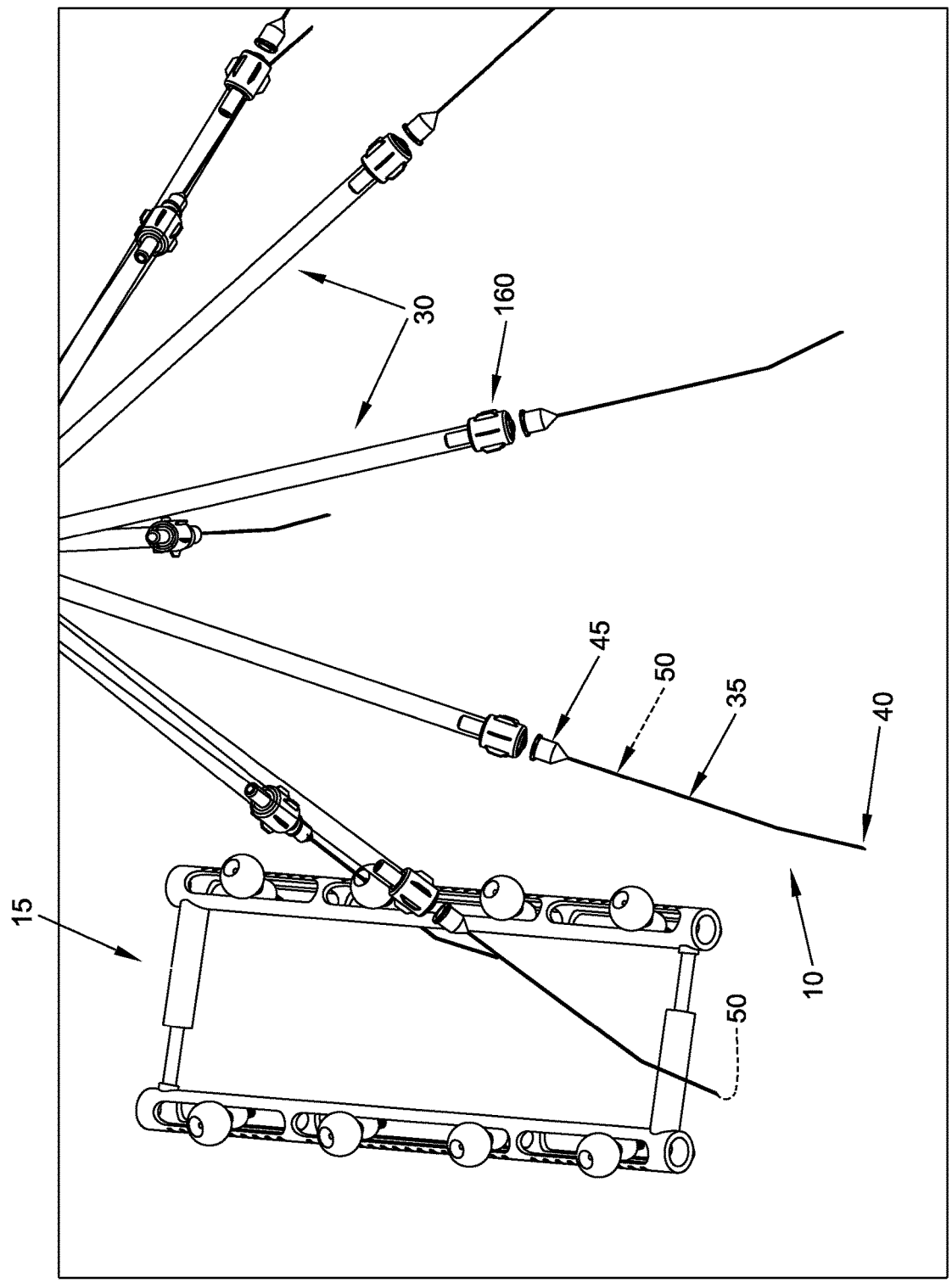
Figure 4:
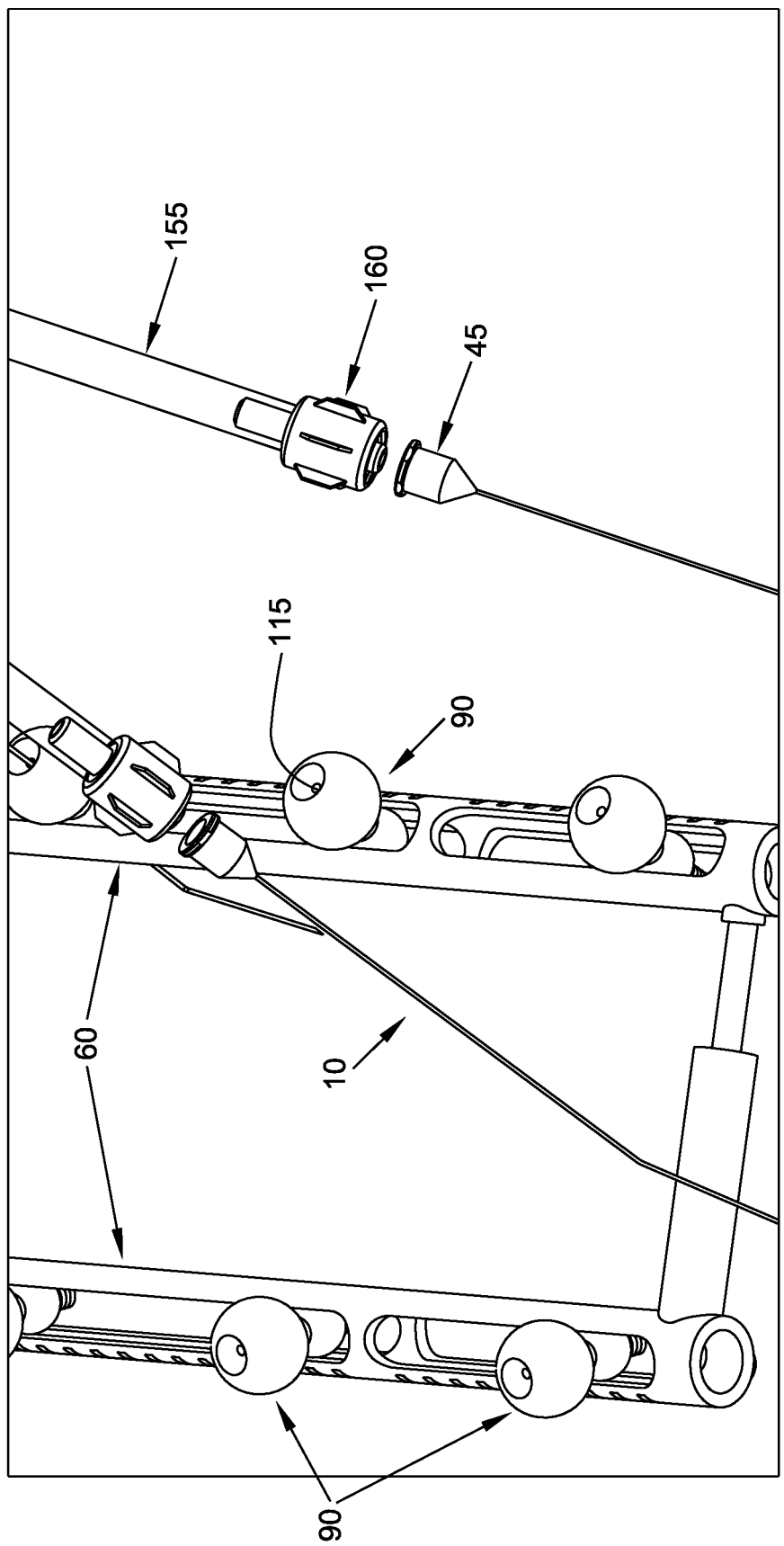
Figure 5:
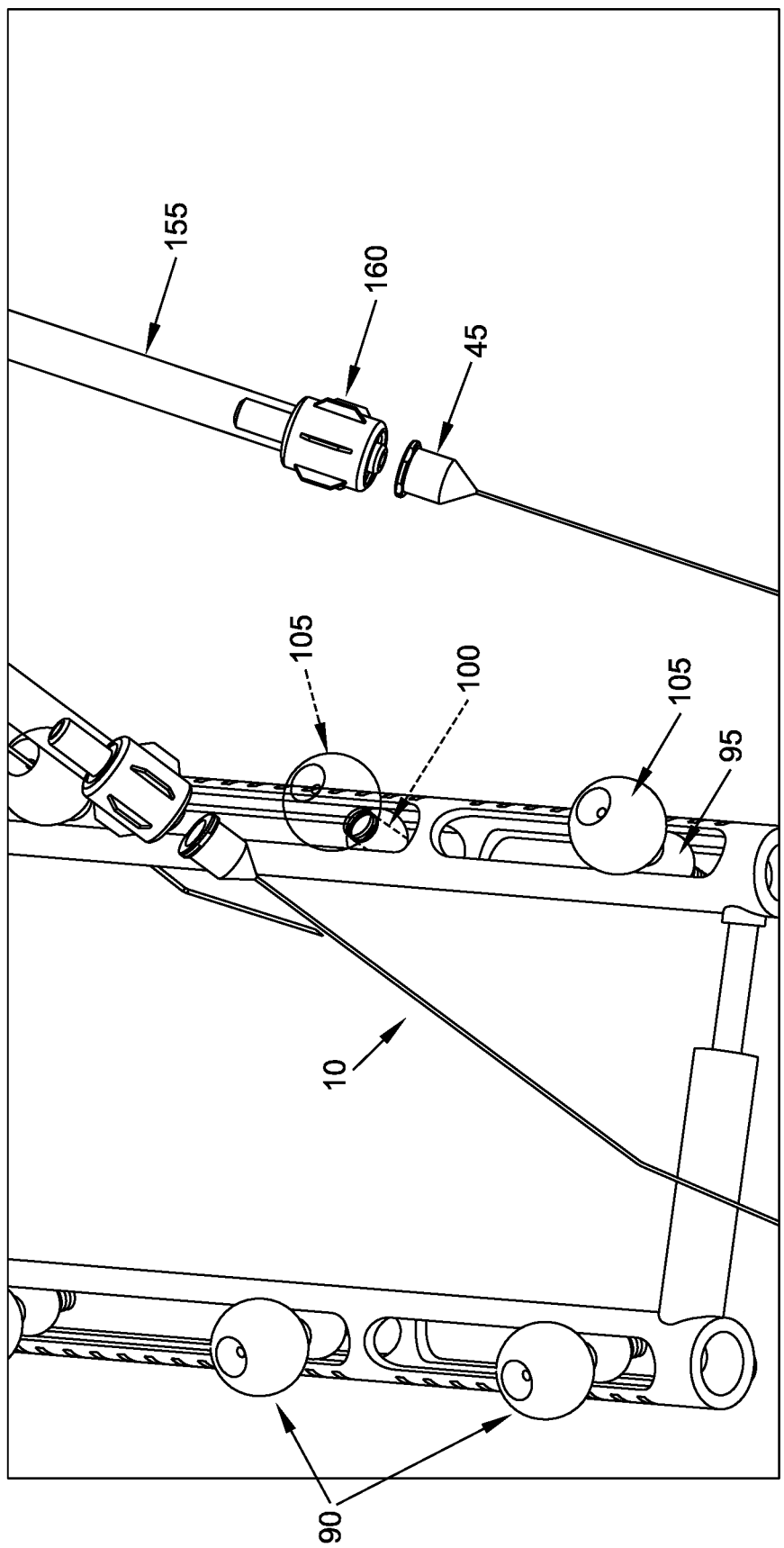
Figure 6:
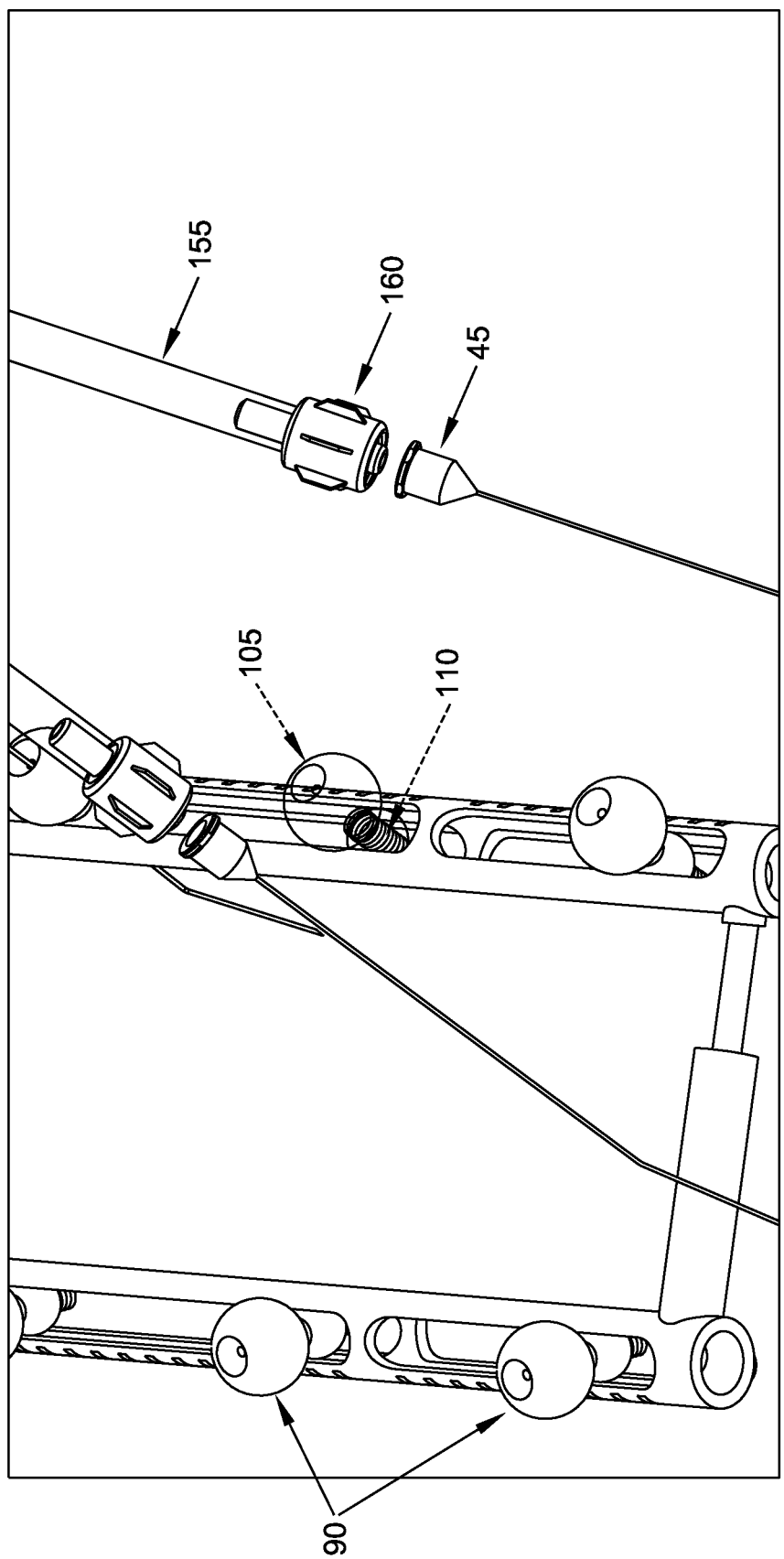
Figure 7:
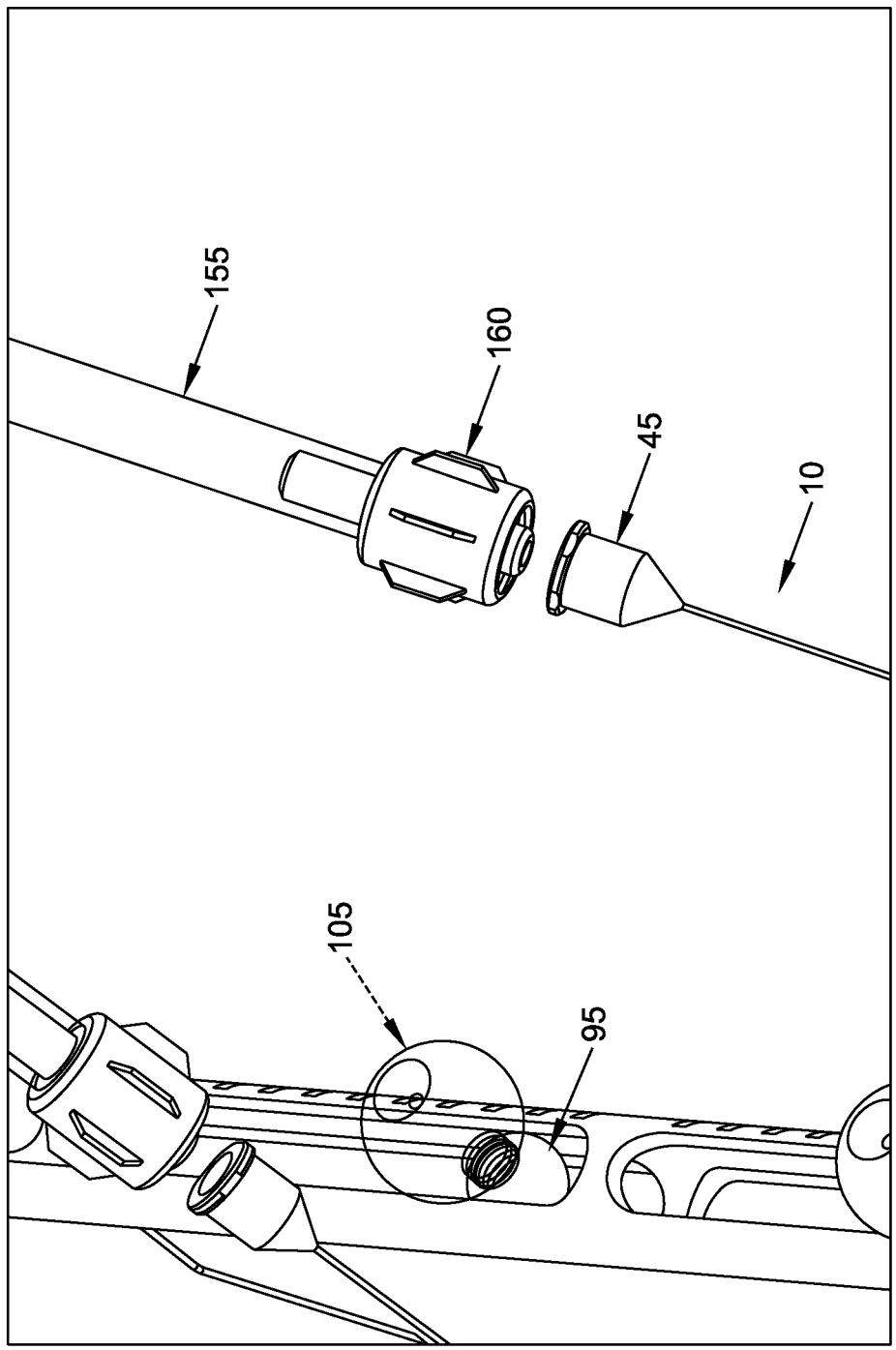
Figure 8:
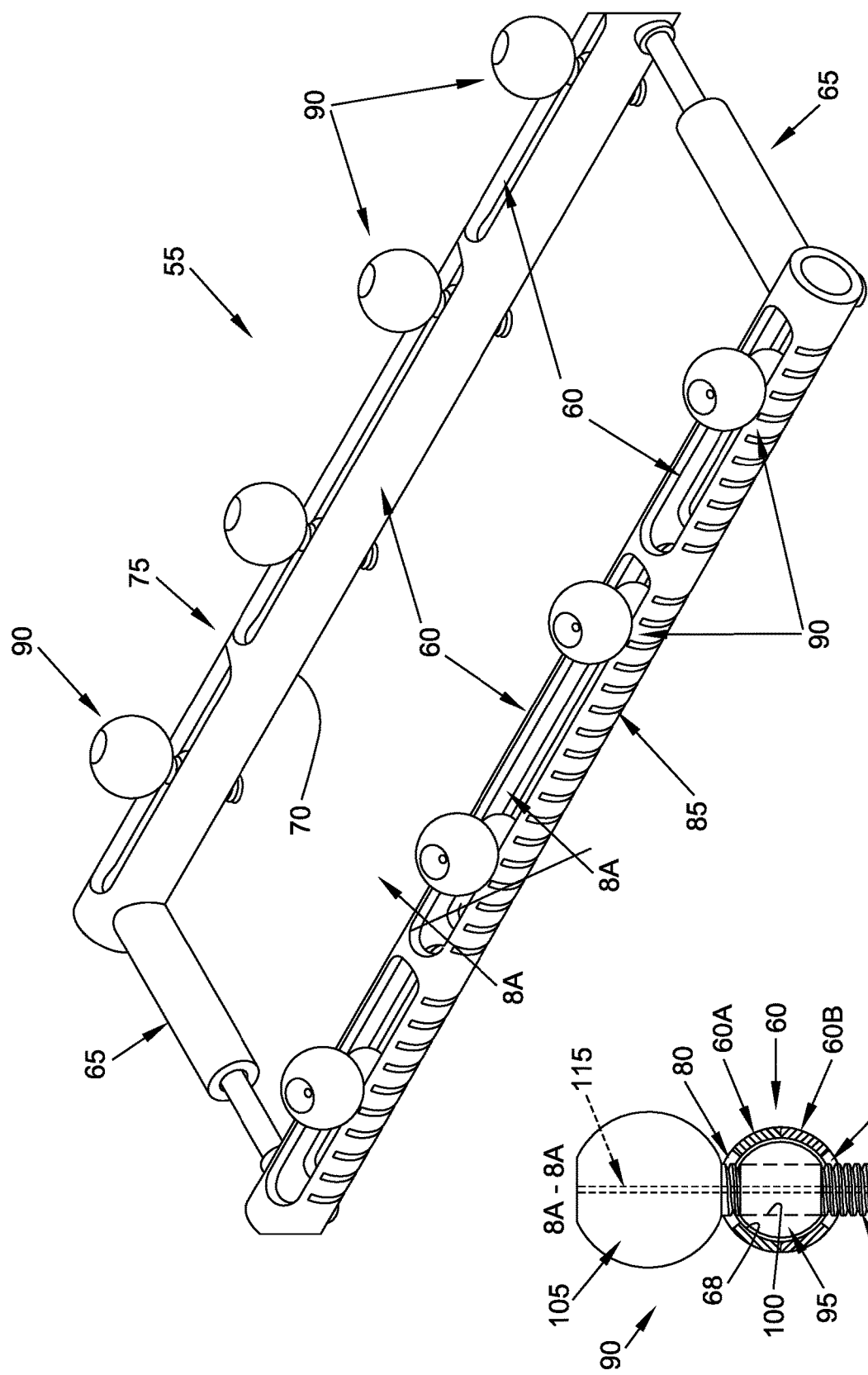
Figure 9:
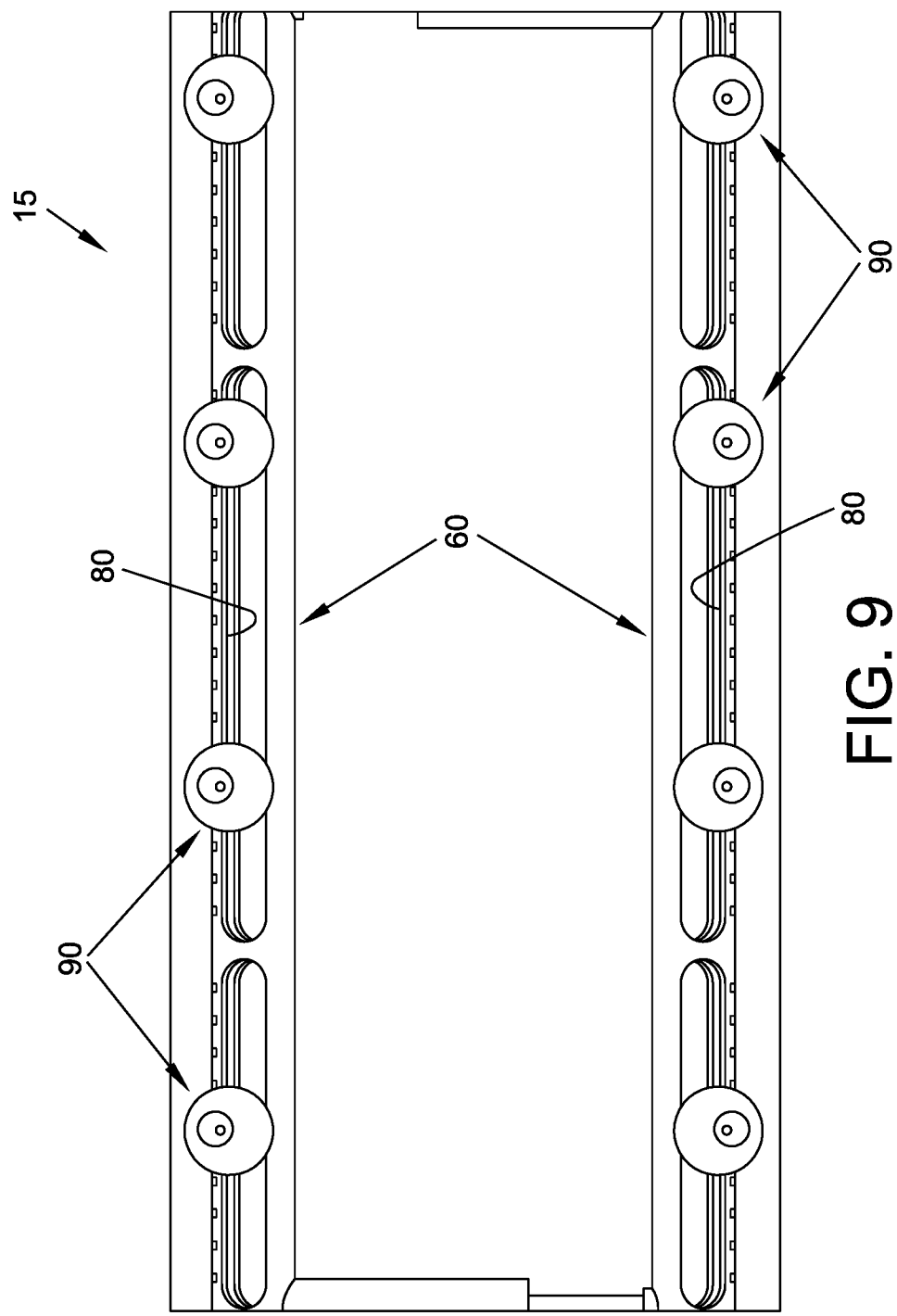
Figure 11:
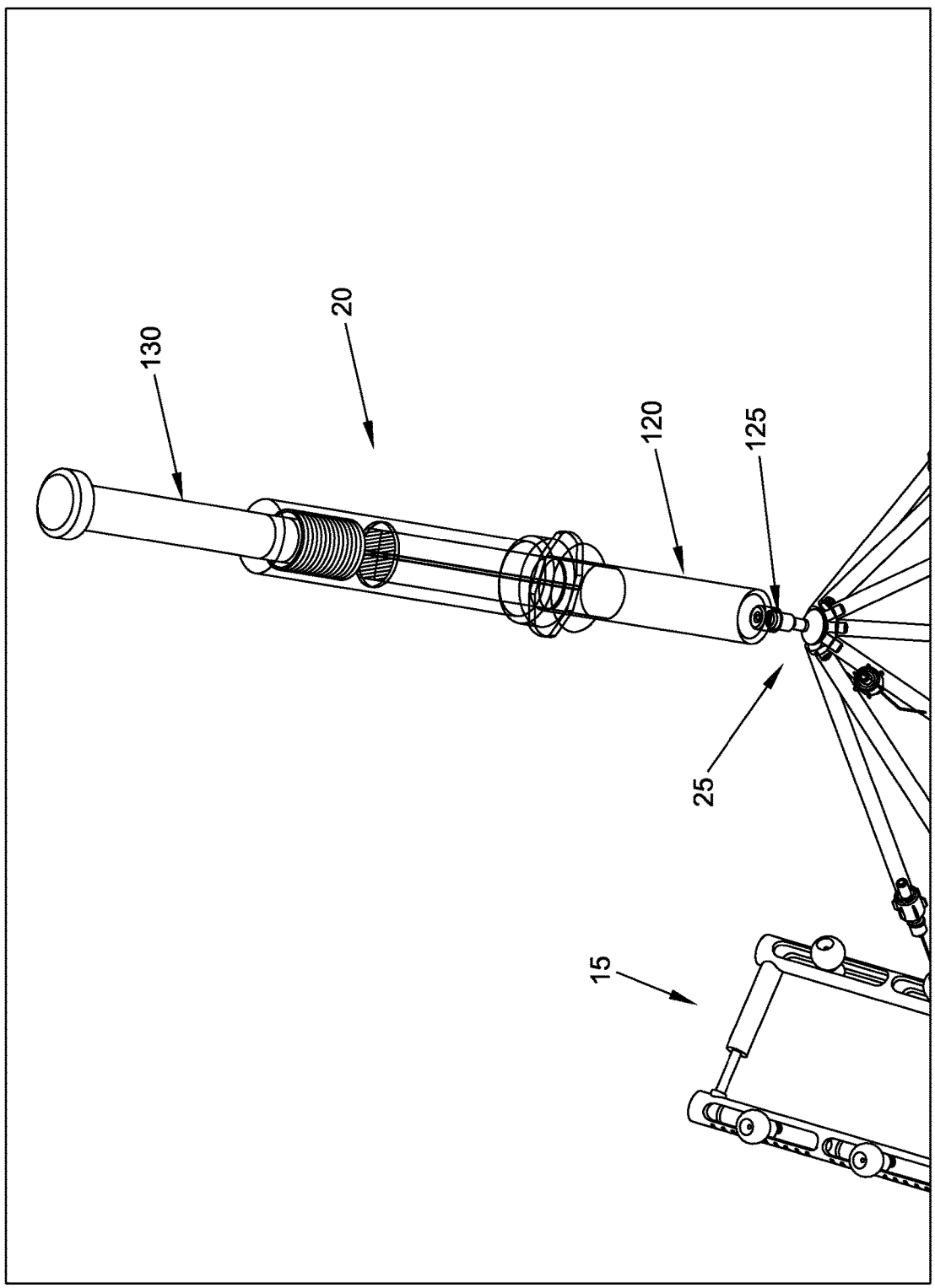

In one form of the invention, the present invention comprises the provision and use of a novel drug delivery system 5 for delivering a drug to the spine of a patient.

Drug Delivery System 5 in General

In one form of the invention, and looking now at FIGS. 1-8, 8A, 9, 10, 10A and 11-19, drug delivery system 5 comprises a plurality of needles 10; a needle guide 15 for guiding and holding the plurality of needles during insertion into the patient's spine; a syringe 20 containing the drug which is to be delivered to the spine of the patient; a port multiplier 25 comprising an inlet port (see below) and a plurality of outlet ports (see below); and a plurality of tubes 30 for providing a connection between the outlet ports of the port multiplier and the plurality of needles.

The Plurality of Needles 10

Each of the plurality of needles 10 comprises a shaft 35 having a sharp distal tip 40 and a hub 45. See FIG. 3. A lumen 50 extends between sharp distal tip 40 and hub 45. Hub 45 is configured for connection to a tube 30, e.g., it may comprise a luer lock connector or another connector of the sort used to connect fluid lines. Shaft 35 may be straight or bent as appropriate.

Needle Guide 15

Needle guide 15 generally comprises a frame 55. Frame 55 preferably comprises two parallel supports 60, which are connected to one another by at least one adjustable arm 65. See FIG. 8. Each parallel support 60 is hollow (i.e., it comprises an interior lumen 68, see FIG. 8A) and comprises a distal surface 70 facing the patient and a proximal surface 75 facing the surgeon. One or more slots 80 are formed in each parallel support 60. Slots 80 open on distal surface 70 and proximal surface 75 and intersect interior lumens 68. The at least one adjustable arm 65 preferably telescopes so as to allow the distance between the two parallel supports 60 to be adjusted. Parallel supports 60 and the at least one adjustable arm 65 are preferably radiolucent, with radiopaque markers 85. By way of example but not limitation, parallel supports 60 and the at least one adjustable arm 65 may be formed out of plastic, and radiopaque markers 85 may comprise a metal coating disposed on parallel supports 60.

A plurality of needle supports 90 (FIG. 8A) are adjustably mounted to interior lumens 68 and slots 80 of parallel supports 60. More particularly, each of the needle supports 90 comprises a spherical body 95 slidably disposed in interior lumens 68 of parallel supports 60. Spherical bodies 95 are sized to be slightly smaller than interior lumens 68 of parallel supports 60 so that spherical bodies 95 can slide along interior lumens 68. At the same time, spherical bodies 95 are sized to be slightly larger than the width of slots 80 such that spherical bodies 95 cannot pass out of slots 80. Each spherical body 95 comprises a threaded bore 100. Each of the needle supports 90 also comprises a body 105 having a threaded projection 110 at its distal end. Threaded projection 110 is sized to extend through slots 80 of parallel supports 60 and make a threaded engagement with threaded bore 100 of spherical body 95. Threaded projection 110 is narrower than slots 80 so that when threaded projection 110 is received by threaded bore 100 of spherical body 95, and body 105 is spaced from proximal surface 75 of parallel support 60, threaded projection 110 can pivot (on rotating spherical body 95) relative to parallel support 60. Body 105 and threaded projection 110 comprise a lumen 115 extending therethrough. Lumen 115 is sized to slidably receive the shaft 35 of a needle 10 so as to guide and support shaft 35 of a needle 10. Note that in an alternative approach for guided delivery, needle supports 90 may be replaced with alternative targeted supports for the guided delivery of devices, e.g., such as the guided delivery of pedicle screws, and/or guidewires for delivering pedicle screws, which may or may not be used with navigation software.

On account of the foregoing construction, when threaded projection 110 is received by threaded bore 100 of spherical body 95, body 105 can be (i) spaced from proximal surface 75 of parallel support 60, whereby to allow needle support 90 to move longitudinally along slot 80 and to pivot relative to the longitudinal axis of parallel support 60, whereby to adjust the location and orientation of lumen 115 of a needle support 90, and (ii) brought into engagement with proximal surface 75 of parallel support 60, whereby to lock needle support 90 in position in slot 80 so as to prevent longitudinal movement of needle support 90 and to prevent pivotal movement of needle support 90 relative to the longitudinal axis of parallel support 60, whereby to fix the location and orientation of lumen 115 of a needle support 90.

In one preferred form of the invention, parallel supports 60 are preferably formed out of two halves 60A, 60B which may be joined together during manufacture, such that spherical bodies 95 of needle supports 90 may be loaded into interior lumens 68 of parallel supports 60 before halves 60A, 60B are joined together.

If desired, needle supports 90 may be formed out of radiolucent materials and, if desired, a radiopaque marker may be disposed on a portion of needle supports 90 to assist in targeting needle supports 90 (e.g., a radiopaque marker may be disposed on the distal end of threaded projection 110).

Syringe 20

Syringe 20 may comprise a standard syringe, e.g., a hollow body 120 having an outlet port 125 and a plunger 130 slidably received in hollow body 120. See FIG. 11. The drug to be delivered to the spine is disposed within hollow body 120, such that distal movement of plunger 130 causes the drug to be ejected out of outlet port 125.

Port Multiplier 25

Port multiplier 25 preferably comprises a hollow body 135 having a single inlet port 140 and a plurality of outlet ports 145, such that a fluid injected into inlet port 140 will be directed out the plurality of outlet ports 145. See FIG. 16. Caps 150 may be provided for selectively closing off individual ones of outlet ports 145. Alternatively and/or additionally, valves 152 may be provided in outlet ports 145 for selectively closing off individual ones of outlet ports 145.

The Plurality of Tubes 30

Figure 12:
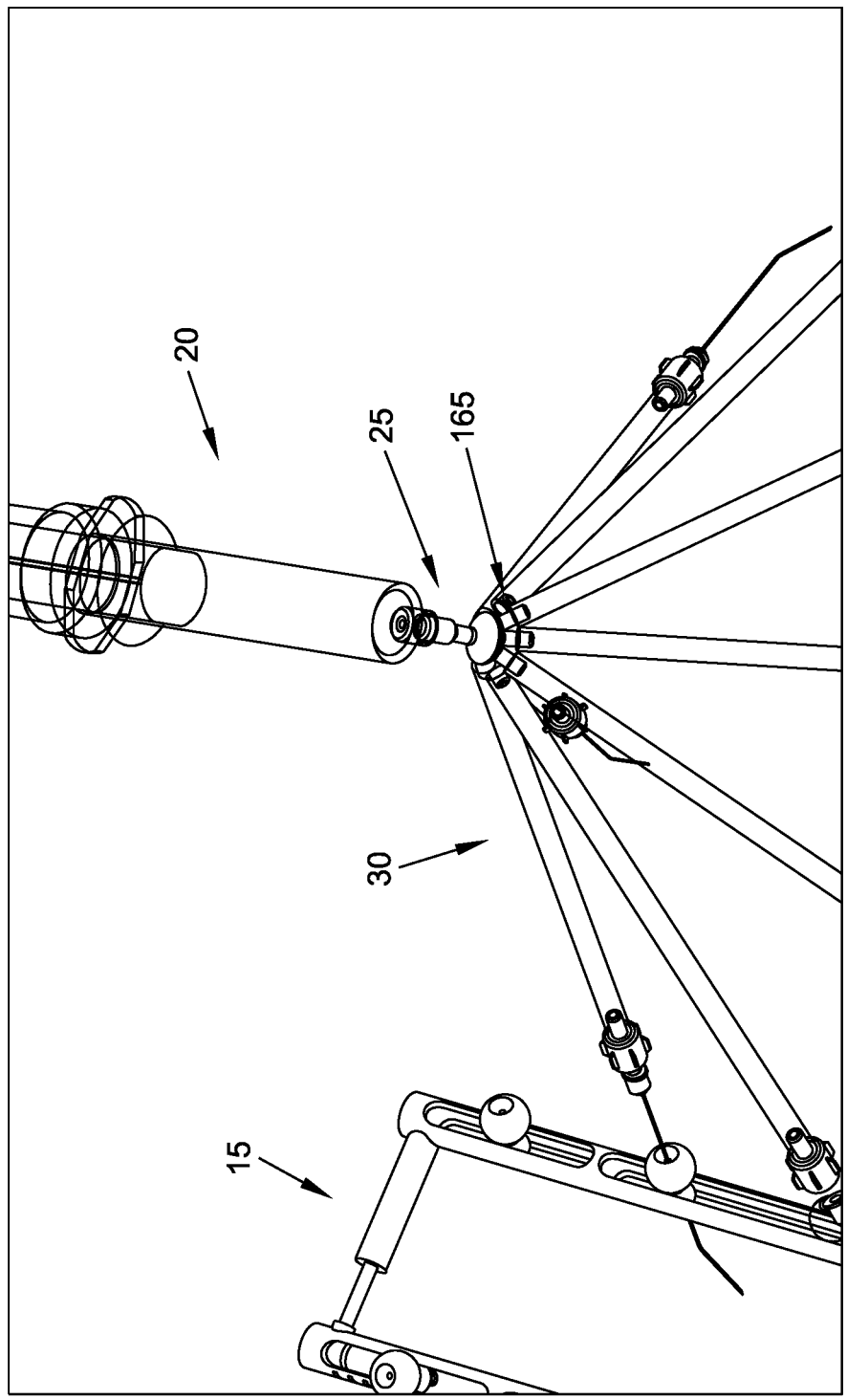
Figure 13:
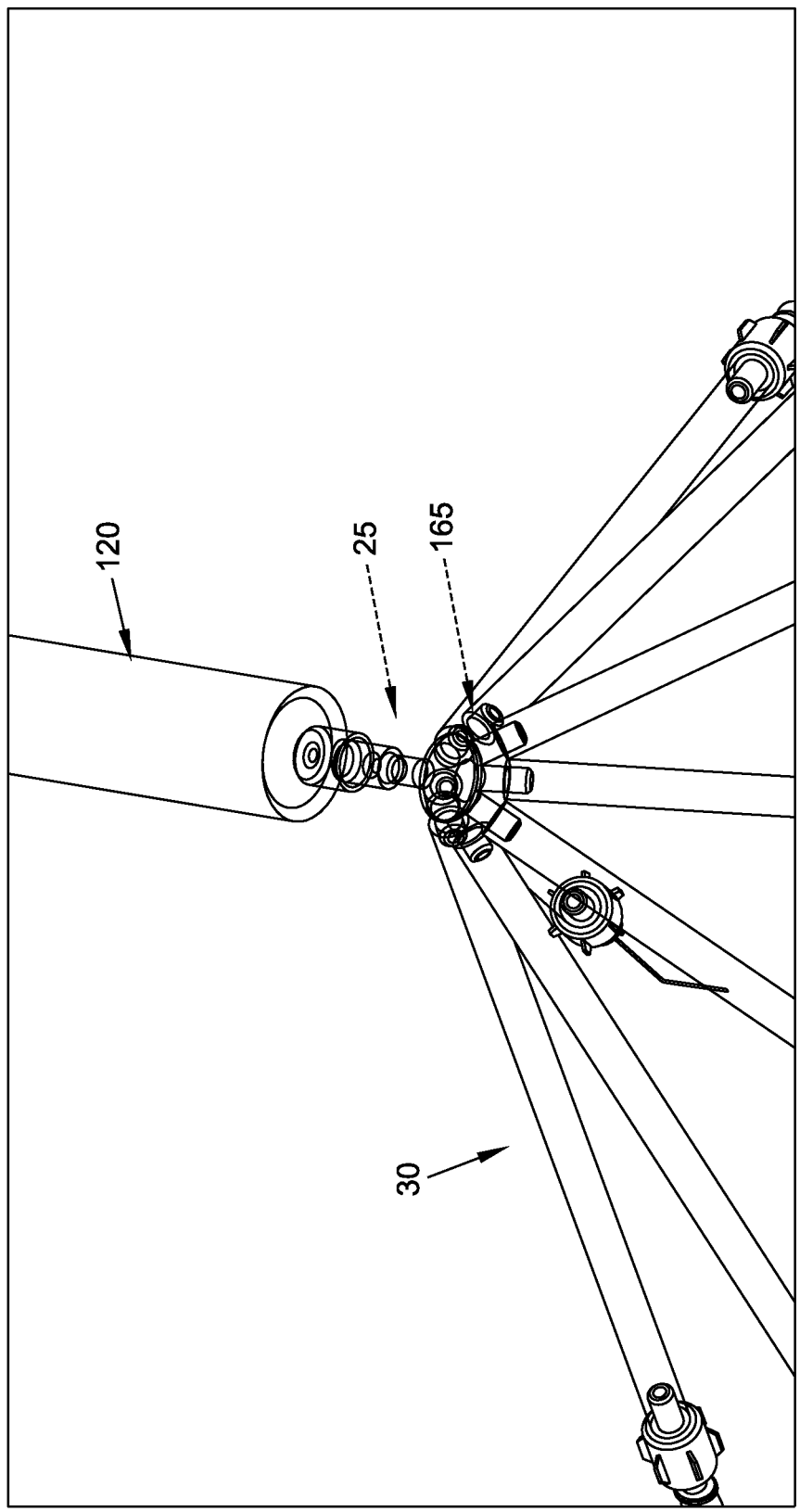
Figure 14:
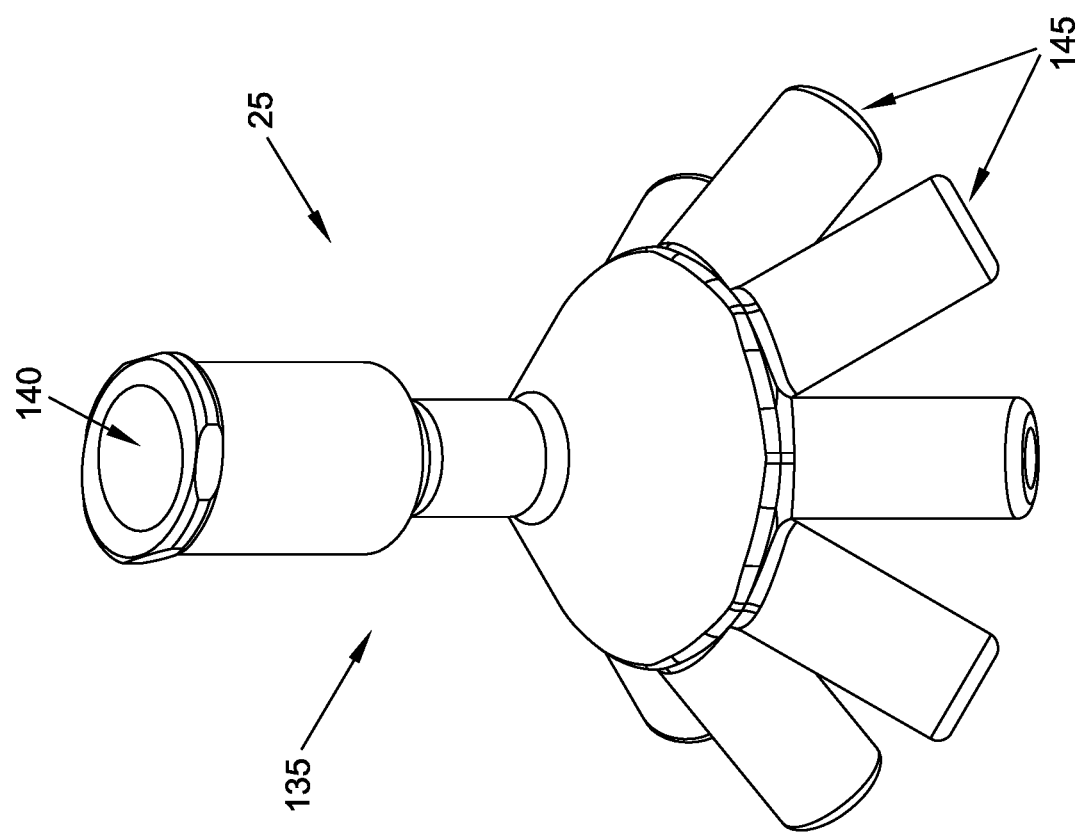
Figure 15:
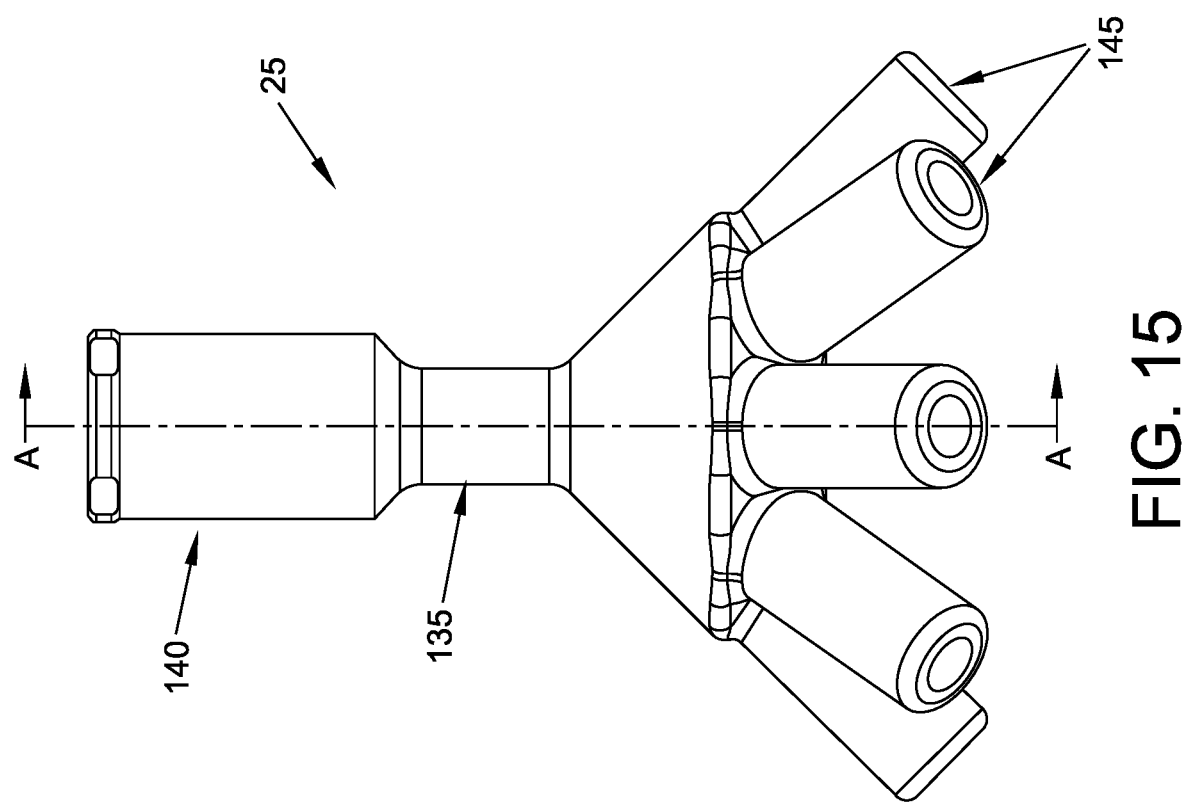
Figure 18:
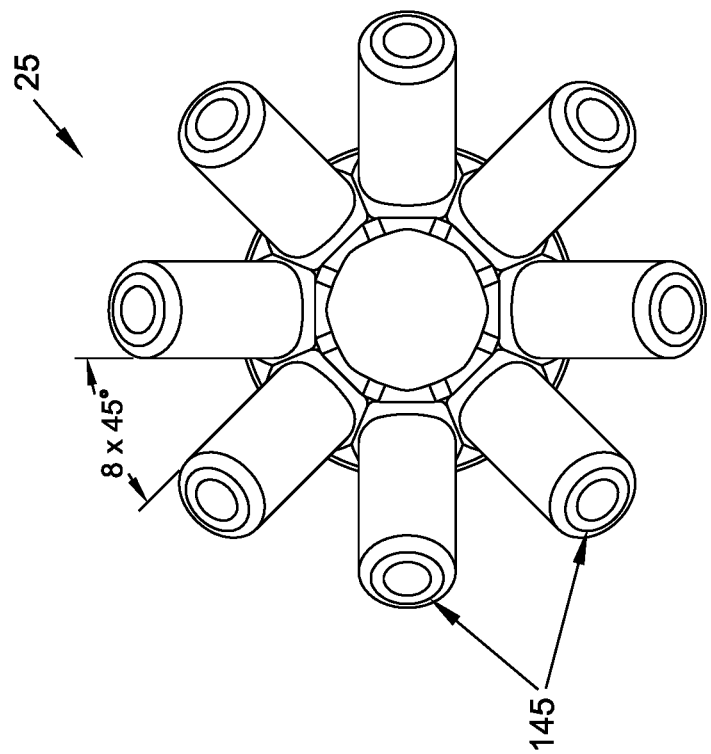
Figure 17:
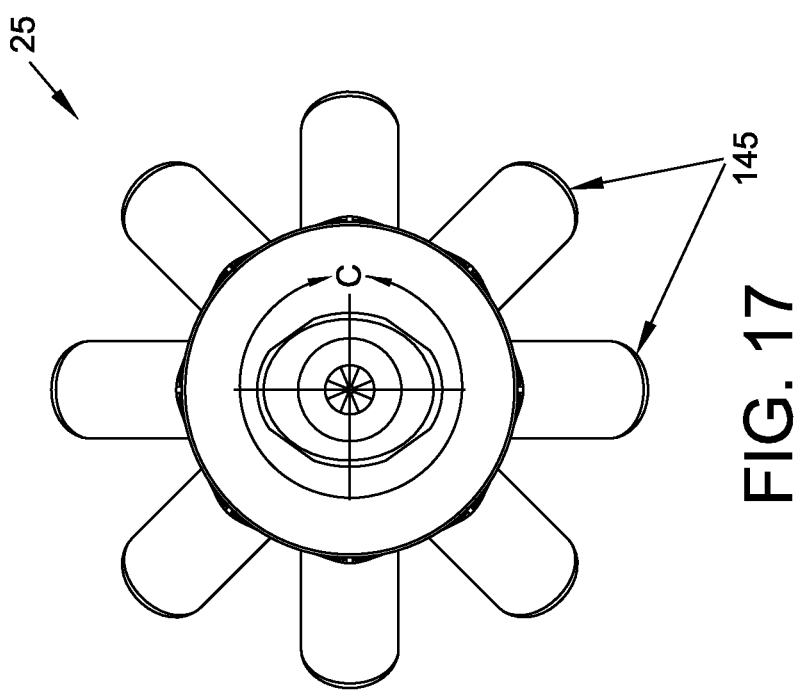
Figure 19:
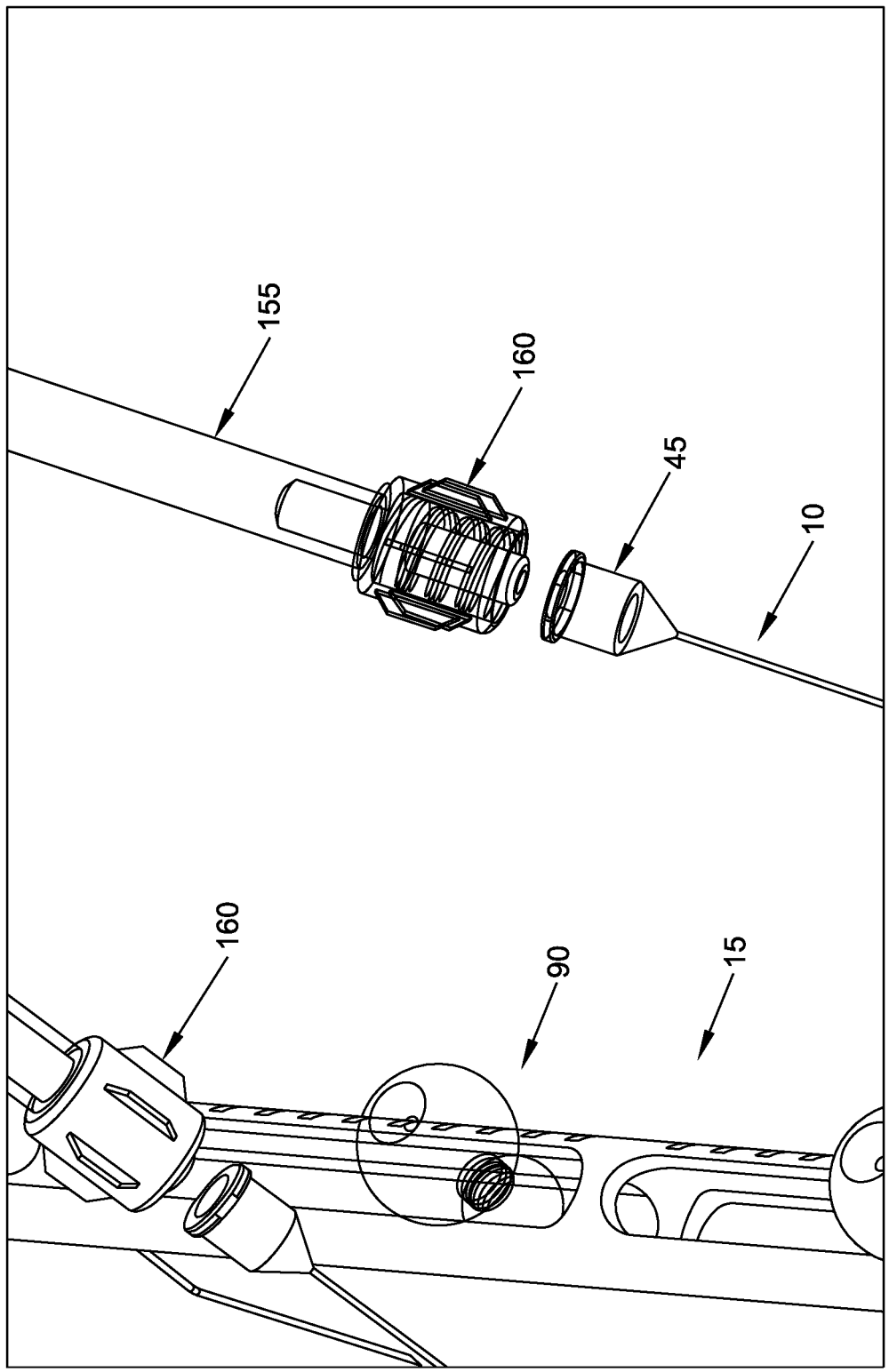
Figure 20G:
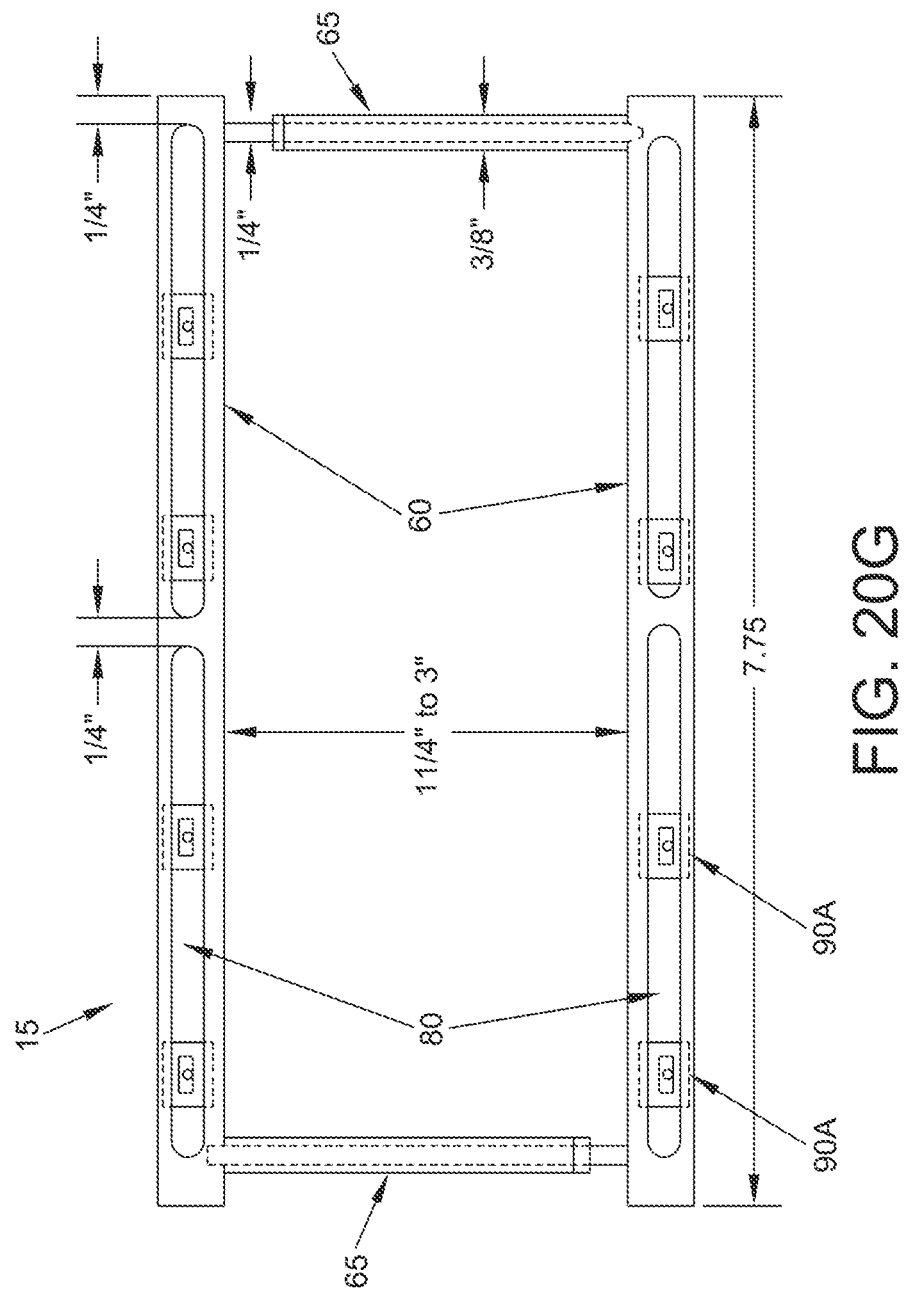

Each of the plurality of tubes 30 comprises a flexible hollow tubular body 155 having a needle connector 160 at one end for connecting with hub 45 of needle 10 (see FIG. 19), and a port multiplier connector 165 at the other end for connecting to an outlet port 145 of port multiplier 25 (see FIG. 12).

Needles 10 being Pre-Fixed to Tubes 30 and/or Tubes 30 being Pre-Fixed to Port Multiplier 25

Note that, if desired, needles 10 may be pre-fixed to tubes 30, and/or tubes 30 may be pre-fixed to outlet ports 145 of port multiplier 25.

Use of Drug Delivery System 5

In use, needle guide 15 is positioned against the skin of the patient adjacent to the spine; needle guide 15 is adjusted so that it can guide the plurality of needles 10 as they are inserted into the spine and hold them in position; port multiplier 25 is connected to syringe 20 containing the drug which is to be delivered; tubes 30 are used to connect the outlet ports 145 of port multiplier 25 to the needles 10; and the syringe 20 is used to eject the drug into port multiplier 25, through tubes 30 and through needles 10 so as to be injected into the desired locations in the spine of the patient.

More particularly, in one preferred form of the invention, drug delivery system 5 may be used as follows.

First, needle guide 15 is positioned against the skin of the patient adjacent to the spine. Adjustable arm 65 is adjusted as necessary so as to position the two parallel supports 60 on either side of the patient's spine. If necessary, frame 55 may be secured to the patient, e.g., with tape, a VELCRO® (hook and loop) strap, etc.

Next, needle guide 15 is used to guide a plurality of needles 10 as they are inserted into the spine and to hold the needles in position. This may be done by loosening a body 105 of a needle support 90 relative to the corresponding spherical body 95 of that needle support 90, sliding the needle support 90 along a slot 80 and adjusting its angular position as necessary, and then advancing a needle 10 through lumen 115 of the needle support 90 so as to advance the needle 10 to the desired location. Preferably this is done using fluoroscopic guidance (e.g., with a needle support in its "loosened" condition, a needle is advanced through the needle support and its position checked using fluoroscopy; if necessary, the needle may be withdrawn and repositioned, until the needle is in its proper position). When needle 10 is properly positioned in the spine, body 105 may be screwed down so as to securely engage parallel support 60, whereby to lock needle support 90 from longitudinal and pivotal motion, thereby keeping needle 10 in proper position. The foregoing process is then repeated for additional needle supports 90 and needles 10 until an appropriate number of needles 10 are properly positioned.

Then inlet port 140 of port multiplier 25 is connected to outlet port 125 of syringe 20 which contains the drug which is to be delivered.

Tubes 30 are then connected to outlet ports 145 of port multiplier 25 and to hubs 45 of needles 10.

Then syringe 20 is used to flow the drug into port multiplier 25, through tubes 30 and through needles 10 so as to be injected into the desired locations in the spine.

Alternative Needle Guide

If desired, needle supports 90 may comprise an alternative construction. More particularly, in this form of the invention, and looking now at FIGS. 20 and 20A-20J, needle supports 90A may be provided. Needle supports 90A generally comprise a tubular body 95A for slidable positioning within lumens 68 of parallel supports 60. Tubular body 95A comprises diametrically-opposed openings 100A. Needle supports 90A also comprise a tapered body 105A for selected disposition in openings 100A of tubular body 95A. Tapered body 105A comprises a lumen 115A.

In this form of the invention, when needle supports 90A are to be movably disposed in lumens 68, tapered body 105A is lightly positioned in openings 100A so as to cause nominal expansion of tubular body 95A. When needle supports 90A are to be locked in position in lumens 68 of parallel supports 60, tapered body 105A is forced distally, whereby to dilate openings 100A and thereby enlarge tubular body 95A, whereby to lock tubular body 95A within lumens 68 of parallel supports 60. Note that tubular bodies 95A extend through slots 80 in parallel supports 60, and needles 10 extend through lumens 115A of tapered bodies 105A.

If desired, needle supports 90A may be formed out of radiolucent materials and, if desired, a radiopaque marker may be disposed on a portion of needle supports 90A to assist in targeting needle supports 90A (e.g., a radiopaque marker may be disposed on the distal end of tapered body 105A).

Spring-Loaded Syringe Assist Device

Figure 21:
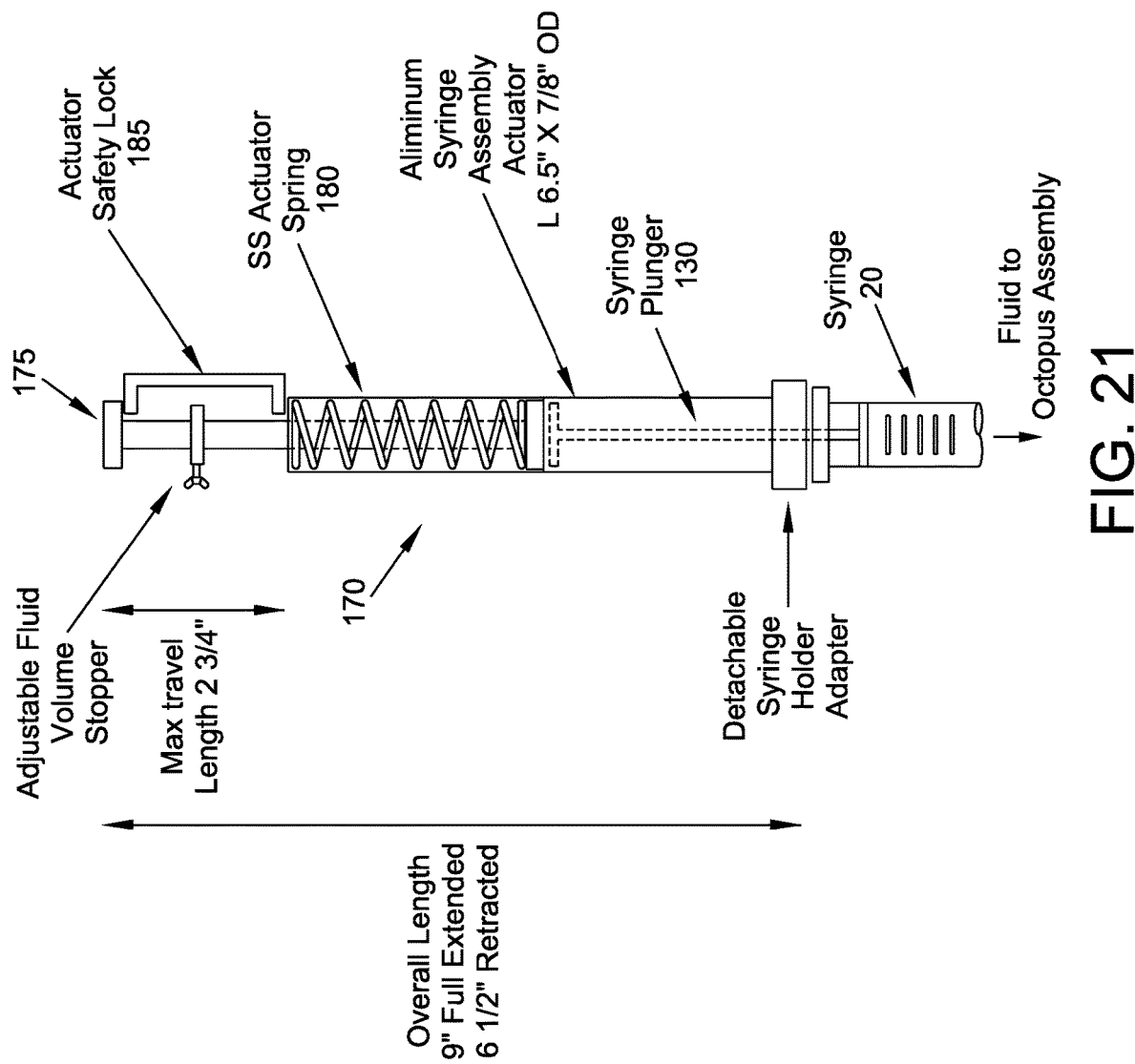
FIG. 21 is a schematic view showing a spring-loaded syringe assist device which may be used with the syringe of the system of the present invention (and/or may be used as an independent syringe assist device for medication delivery to patients)

In another form of the invention, and looking now at FIG. 21, a spring-loaded syringe assist device 170 may be provided to power distal movement of plunger 130 of syringe 20. More particularly, in this form of the invention, spring-loaded syringe assist device 170 comprises an assist plunger 175 which engages plunger 130 of syringe. Assist plunger 175 is powered by a spring 180. An actuator safety lock 185 is provided to prevent assist plunger 175 from moving under the influence of spring 180 until actuator safety lock 185 is removed.

In this form of the invention, in use, spring-loaded syringe assist device 170 is mounted to the proximal end of syringe 20 so that assist plunger 175 engages plunger 130 of syringe 20, and then, when the drug is to be deployed, actuator safety lock 185 is removed, whereupon spring 180 causes assist plunger 175 of spring-loaded syringe assist device 170 to drive plunger 130 of syringe 20 distally, whereby to dispense the drug in syringe 20.

If desired, and looking now at FIG. 21A, spring-loaded syringe assist device 170 may be provided with a brake lever 186 for increased control of dispensing the drug in syringe 20.

More particularly, brake lever 186 comprises a spring arm 187 which normally holds a finger 188 in engagement with teeth 175A on assist plunger 175 of spring-loaded syringe assist device 170, whereby to lock assist plunger 175 against axial movement. Squeezing spring arm 187 (e.g., between the thumb and forefinger of a user) withdraws finger 188 from engagement with teeth 175A on assist plunger 175, whereby to enable assist plunger 175 to move axially under the power of the aforementioned spring 180.

In use, spring-loaded syringe assist device 170 is mounted to syringe 20 by positioning the finger grips of the syringe in slots 189 at the base of spring-loaded syringe assist device 170 with plunger 130 of syringe 20 being disposed within the body of spring-loaded syringe assist device 170, adjacent to the distal end of assist plunger 175. When the drug is to be dispensed from syringe 20, spring arm 187 is squeezed so as to withdraw finger 188 from engagement with teeth 175A of assist plunger 175, whereby to "unlock" assist plunger 175 of spring-loaded syringe assist device 170 so that assist plunger 175 can move distally under the power of spring 180, whereby to dispense the drug in syringe 20. When the desired amount of the drug has been dispensed, spring arm 187 is released so as to cause finger 188 to re-engage teeth 175A of assist plunger 175, whereby to "lock" assist plunger 175 of spring-loaded syringe assist device 170 from further distal movement under the power of spring 180. If and when additional drug is to be dispensed from syringe 20, spring arm 187 is squeezed again so as to withdraw finger 188 from engagement with teeth 175A of assist plunger 175, whereby to "unlock" assist plunger 175 of spring-loaded syringe assist device 170 so that assist plunger 175 can move distally under the power of spring 180, whereby to dispense the drug in syringe 20. When an appropriate amount of the drug has been dispensed, spring arm 187 is released so as to "lock" assist plunger 175 against further movement.

It should also be appreciated that, if desired, the spring 180 of spring-loaded syringe assist device 170 may be replaced by a powered mechanism, e.g., an electrical motor.

Filling Syringe 20

Figure 22:
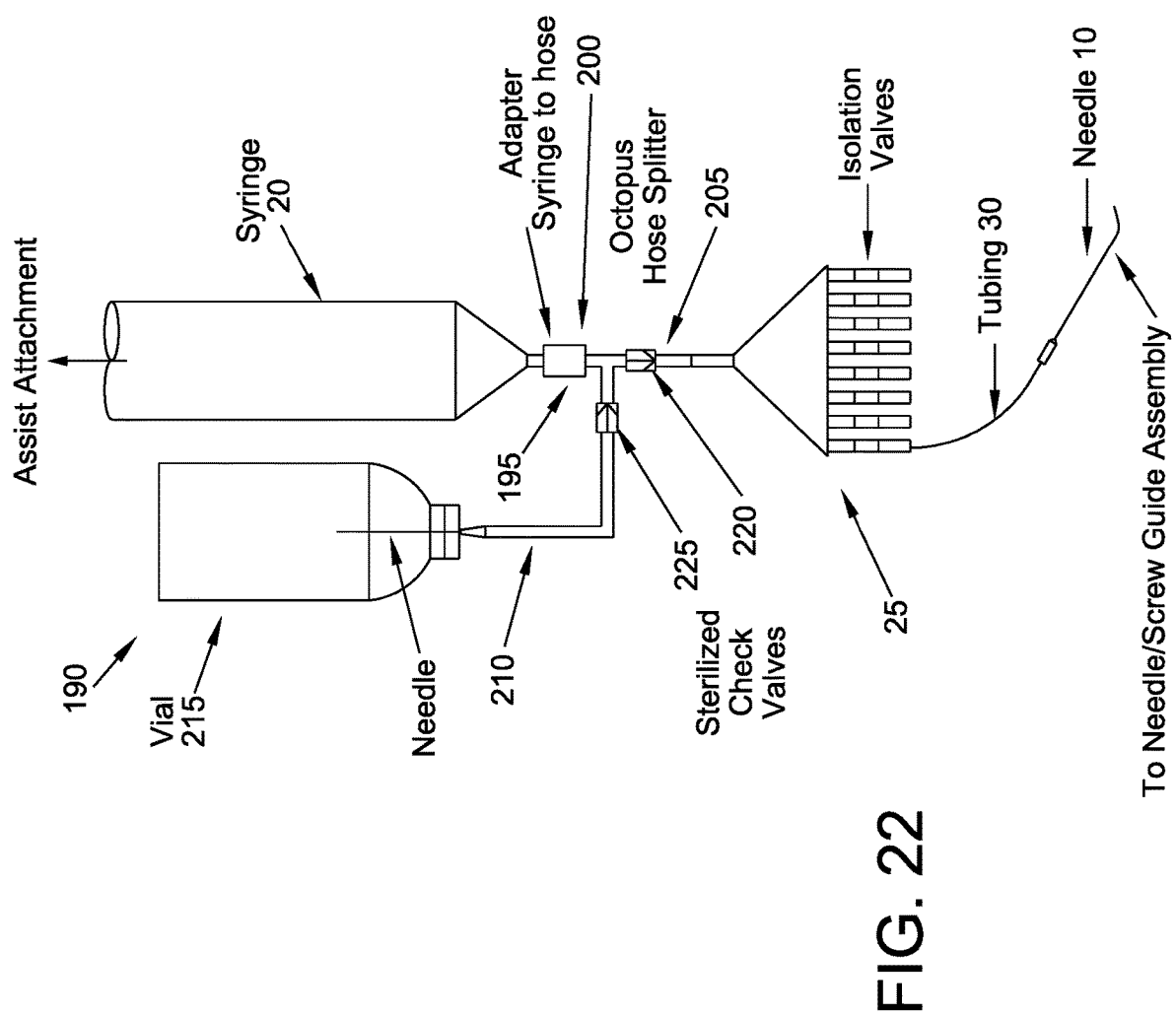
FIG. 22 is a schematic view showing a vial adapter which may be used with the system of the present invention.

In many cases, syringe 20 may be pre-filled with the drug which is to be injected into the spine. However, if desired, syringe 20 may be filled at the time of use. In this case, and looking now at FIG. 22, it can be desirable to interpose a vial adapter 190 between the outlet port 125 of syringe 20 and inlet port 140 of port multiplier 25. Vial adapter 190 preferably comprises a T-shaped hollow body 195 having a first port 200 connectable to the outlet port 125 of syringe 20, a second port 205 connectable to the inlet port 140 of port multiplier 25, and a needle line 210 connectable to a vial 215. A check valve 220 is provided in T-shaped hollow body 195 at second port 205, and a check valve 225 is provided in T-shaped hollow body 195 at needle line 210. Check valve 220 allows fluid to flow from T-shaped hollow body 195 to port multiplier 25 but prevents fluid from flowing from port multiplier 25 into T-shaped hollow body 195. Check valve 225 allows fluid to flow from needle line 210 into T-shaped hollow body 195 but prevents fluid from flowing from T-shaped hollow body 195 into needle line 210.

When syringe 20 is to be loaded from vial 215, plunger 130 is drawn proximally so as to create suction at outlet port 125 of syringe 20. Check valve 225 allows the drug in vial 215 to be drawn into syringe 20, with check valve 220 preventing air from passing out of port multiplier 25 and into syringe 20. When the drug is to be dispensed from syringe 20, plunger 130 is moved distally. When this occurs, check valve 220 prevents the drug exiting outlet port 125 of syringe 20 from re-entering needle line 210, and check valve 225 allows the drug to pass into port multiplier 25.

Use of the System to Deliver Other Materials

In the foregoing disclosure, the system of the present invention is discussed in the context of delivering drugs (e.g., analgesics) to the spine of the patient. However, it should be appreciated that the present invention may also be used for delivering other materials (e.g., non-drug fluids including biologics, etc.) to the spine of a patient.

Use of Needle Guide 15 for Deploying Other Objects into the Body of a Patient It should be appreciated that the present invention may also be used in medical procedures which require targeted deployment of objects into the spine or other anatomy of a patient.

By way of example but not limitation, needle guide 15 may be used to deploy pedicle screws into the spine of a patient. More particularly, in this form of the invention, needle guide 15 may be used, with fluoroscopic imaging, or navigation software, to set a plurality of guidewires into the pedicles of the spine. Once one or more guidewires have been targeted into the pedicles of the spine using needle guide 15, the needle guide may be removed and then pedicle screws may be moved down the guidewires and advanced into the pedicles of the spine.

By way of further example but not limitation, needle guide 15 may be used to deploy bone implants into the spine of a patient.

By way of still further example but not limitation, needle guide 15 may be used to deploy radiofrequency (RF) ablation probes into the spine of a patient for the targeted ablation of tissue.

And by way of further example but not limitation, needle guide 15 can be used to deploy sensory nerve stimulator (SNS) leads into the spine of a patient for the targeted application of pain-relieving electrical stimulation.

It will be appreciated by those skilled in the art that the present invention may also be used in many other situations which require targeted deployment of objects into the anatomy of a patient.

Needle Supports 90 with Reduced Degrees of Freedom

In the foregoing sections, needle supports 90 are disclosed as being, in their unlocked configuration, axially movable along parallel supports 60 and rotationally movable about the longitudinal axes of parallel supports 60. However, it should be appreciated that, if desired, needle supports 90 may be provided with reduced degrees of freedom.

By way of example but not limitation, needle supports 90 may be configured so that, in their unlocked configuration, needle supports 90 are axially movable along parallel supports 60 but not rotationally movable about the longitudinal axes of parallel supports 60.

By way of further example but not limitation, needle supports 90 may be configured so that, in their unlocked configuration, needle supports 90 are rotationally movable about the longitudinal axes of parallel supports 60 but not axially movable along parallel supports 60.

By way of still further example but not limitation, needle supports 90 may be axially and rotationally fixed relative to parallel supports 60.

It should be further appreciated that various means may be used to mount needle supports 90 to parallel supports 60, e.g., screw mounts, clamp mounts, press fit mounts, glide fit mounts, magnetic mounts, etc.

Use of the System in the Veterinary Space

While the primary application for the novel delivery system of the present invention is intended to be for human use, it should also be appreciated that the novel delivery system may also be used in veterinary applications.

Modifications of the Preferred Embodiments

It should be understood that many additional changes in the details, materials, steps and arrangements of parts, which have been herein described and illustrated in order to explain the nature of the present invention, may be made by those skilled in the art while still remaining within the principles and scope of the invention.

What is claimed is:

1. A drug delivery system comprising:
   a plurality of needles;
   a needle guide for guiding and holding the plurality of needles during insertion into a patient's spine;
   a syringe containing a drug which is to be delivered into the patient's spine;
   a port multiplier comprising an inlet port connectable to the syringe and a plurality of outlet ports; and
   a plurality of tubes for providing fluid connections between the plurality of outlet ports of the port multiplier and the plurality of needles;
   wherein the needle guide comprises:
      a frame comprising two frame supports connected to one another by at least one adjustable arm, wherein each of the frame supports comprises a frame lumen and a pair of slots communicating with the frame lumen; and
      a plurality of needle supports selectively movably mounted to the frame, wherein each of the needle supports is configured to guide and hold a needle of the plurality of needles during insertion into the patient's spine;
   wherein each of the needle supports is reconfigurable between (i) a first configuration wherein each needle support is movable axially along the frame and rotatable relative to the frame; and (ii) a second configuration wherein each needle support is axially and rotatably fixed relative to the frame; and
   wherein each of the needle supports comprises:
      a spherical body slidably disposed in the frame lumen of each frame support, wherein the spherical body comprise a threaded bore; and
      a body having a threaded projection sized to pass through each slot in either frame support and to be threadingly received in the threaded bore of the spherical body, wherein the threaded projection has a width less than a width of each slot formed in either frame support, and further wherein a needle lumen extends through the body and the threaded projection, the needle lumen being sized to slidably receive and support one of the plurality of needles;
   such that (i) the body can be spaced from either frame support, whereby to allow each needle support to move longitudinally within the frame lumen of either frame support and to pivot relative to a longitudinal axis of either frame support; and (ii) the body can be brought into engagement with either frame support, whereby to lock each needle support against longitudinal movement and to prevent pivotal movement of each needle support.

2. The drug delivery system according to claim 1 wherein the frame supports are formed out of a radiolucent material, and further wherein radiopaque markers are disposed on the frame supports.

3. The drug delivery system according to claim 1 wherein the plurality of needle supports are formed out of a radiolucent material, and further wherein radiopaque markers are disposed on the plurality of needle supports.

4. The drug delivery system according to claim 1 further comprising a spring-loaded syringe assist device for operating the syringe.

5. The drug delivery system according to claim 4 wherein the syringe comprises (a) a syringe body having a cavity containing the drug and an output port, and (b) a plunger movably disposed in the cavity for driving the drug out of the output port, and further wherein the spring-loaded syringe assist device comprises:
 a housing for mounting to the syringe body;
 a driver for engaging the plunger and moving the plunger so as to drive the drug contained in the cavity out of the output port; and
 a power unit for moving the driver.

6. The drug delivery system according to claim 5 wherein the power unit comprises a spring.

7. The drug delivery system according to claim 6 wherein the spring-loaded syringe assist device further comprises a member for releasably holding the spring in an energized condition.

8. The drug delivery system according to claim 1 wherein the port multiplier comprises:
 a hollow body having an interior;
 an input port in fluid communication with the interior of the hollow body, the input port being configured for attachment to the syringe containing a drug; and
 a plurality of output ports in fluid communication with the interior of the hollow body, each of the plurality of output ports being configured for attachment to a fluid line comprising a needle of the plurality of needles.

9. The drug delivery system according to claim 8 wherein each of the plurality of output ports comprises a valve for selectively closing off each of the plurality of output ports.

10. A drug delivery system comprising:
 a plurality of needles;
 a needle guide for guiding and holding the plurality of needles during insertion into a patient's spine;
 a syringe containing a drug which is to be delivered into the patient's spine;
 a port multiplier comprising an inlet port connectable to the syringe and a plurality of outlet ports; and
 a plurality of tubes for providing fluid connections between the plurality of outlet ports of the port multiplier and the plurality of needles;
 wherein the needle guide comprises:
  a frame comprising two frame supports connected to one another by at least one adjustable arm, wherein each of the frame supports comprises a frame lumen and a pair of slots communicating with the frame lumen; and
  a plurality of needle supports selectively movably mounted to the frame, wherein each of the needle supports is configured to guide and hold a needle of the plurality of needles during insertion into the patient's spine;
 wherein each of the needle supports is reconfigurable between (i) a first configuration wherein each needle support is movable axially along the frame and rotatable relative to the frame; and (ii) a second configuration wherein each needle support is axially and rotatably fixed relative to the frame; and
 wherein each of the needle supports comprises:
  a tubular body slidably disposed in the frame lumen of either frame support, wherein the tubular body comprises a pair of diametrically-opposed openings; and
  a tapered member having a first portion smaller than the pair of diametrically-opposed openings and a second portion larger than the pair of diametrically-opposed openings, and a needle lumen extending through the tapered member, the needle lumen being sized to slidably receive and support one of the plurality of needles;
  such that (i) the first portion of the tapered member can be disposed in the pair of diametrically-opposed openings, whereby to allow the tubular body to move longitudinally within the frame lumen of either frame support and to rotate relative to a longitudinal axis of either frame support; and (ii) the second portion of the tapered member can be disposed in the pair of diametrically-opposed openings, whereby to lock the tubular body against longitudinal movement and to prevent rotational movement of the tubular body.

11. The drug delivery system according to claim 10 wherein the frame supports are formed out of a radiolucent material, and further wherein radiopaque markers are disposed on the frame supports.

12. The drug delivery system according to claim 10 wherein the plurality of needle supports are formed out of a radiolucent material, and further wherein radiopaque markers are disposed on the plurality of needle supports.

13. The drug delivery system according to claim 10 further comprising a spring-loaded syringe assist device for operating the syringe.

14. The drug delivery system according to claim 13 wherein the syringe comprises (a) a syringe body having a cavity containing the drug and an output port, and (b) a plunger movably disposed in the cavity for driving the drug out of the output port, and further wherein the spring-loaded syringe assist device comprises:
 a housing for mounting to the syringe body;
 a driver for engaging the plunger and moving the plunger so as to drive the drug contained in the cavity out of the output port; and
 a power unit for moving the driver.

15. The drug delivery system according to claim 14 wherein the power unit comprises a spring.

16. The drug delivery system according to claim 15 wherein the spring-loaded syringe assist device further comprises a member for releasably holding the spring in an energized condition.

17. The drug delivery system according to claim 10 wherein the port multiplier comprises:
 a hollow body having an interior;
 an input port in fluid communication with the interior of the hollow body, the input port being configured for attachment to the syringe containing the drug; and
 a plurality of output ports in fluid communication with the interior of the hollow body, each of the plurality of output ports being configured for attachment to a fluid line comprising a needle of the plurality of needles.

18. The drug delivery system according to claim 17 wherein each of the plurality of output ports comprises a valve for selectively closing off each of the plurality of output ports.

19. A method for delivering a drug, the method comprising:
   providing a drug delivery system comprising:
      a plurality of needles;
      a needle guide for guiding and holding the plurality of needles during insertion into a patient's spine;
      a syringe containing the drug which is to be delivered into the patient's spine;
      a port multiplier comprising an inlet port connectable to the syringe and a plurality of outlet ports; and
      a plurality of tubes for providing fluid connections between the plurality of outlet ports of the port multiplier and the plurality of needles;
      wherein the needle guide comprises:
         a frame comprising two frame supports connected to one another by at least one adjustable arm, wherein each of the frame supports comprises a frame lumen and a pair of slots communicating with the frame lumen; and
         a plurality of needle supports selectively movably mounted to the frame, wherein each of the needle supports is configured to guide and hold a needle of the plurality of needles during insertion into the patient's spine; and
      wherein each of the needle supports comprises:
         a spherical body slidably disposed in the frame lumen of either frame support, wherein the spherical body comprises a threaded bore; and
         a body having a threaded projection sized to pass through each slot in either frame support and to be threadingly received in the threaded bore of the spherical body, wherein the threaded projection has a width less than a width of each slot formed in either frame support, and further wherein a needle lumen extends through the body and the threaded projection, the needle lumen being sized to slidably receive and support one needle of the plurality of needles;
         such that (i) the body can be spaced from either frame support, whereby to allow each needle support to move longitudinally within the frame lumen and to pivot relative to a longitudinal axis of either frame support; and (ii) the body can be brought into engagement with either frame support, whereby to lock each needle support against longitudinal movement and to prevent pivotal movement of each needle support;
   positioning the needle guide against the skin of the patient adjacent to the patient's spine;
   using the needle guide to guide the plurality of needles as the plurality of needles are inserted into the patient's spine and hold the plurality of needles in position;
   connecting the port multiplier to the syringe containing the drug which is to be delivered;
   connecting the plurality of tubes to the plurality of outlet ports of the port multiplier and to the plurality of needles; and
   using the syringe to eject the drug into the port multiplier, through the plurality of tubes and through the plurality of needles so as to be injected into the desired locations in the patient's spine.

20. The method according to claim 19 wherein each of the needle supports is reconfigurable between (i) a first configuration wherein each needle support is movable axially along the frame and rotatable relative to the frame; and (ii) a second configuration wherein each needle support is axially and rotatably fixed relative to the frame.

21. The method according to claim 20 wherein one needle of the plurality of needles is inserted through one needle support of the plurality of needle supports and into the patient's spine while the one needle support of the plurality of needle supports is in the first configuration, the one needle of the plurality of needles has a disposition checked and corrected as necessary while the one needle support of the plurality of needle supports is in the first configuration, and then the one needle support of the plurality of needle supports is reconfigured into the second configuration while the one needle of the plurality of needles remains inserted into the patient's spine, with the foregoing process thereafter repeated for at least one other of the plurality of needles.

22. The method according to claim 21 wherein the one needle of the plurality of needles has the disposition checked and corrected as necessary using fluoroscopy.

23. The method according to claim 19 wherein the frame supports are formed out of a radiolucent material, and further wherein radiopaque markers are disposed on the frame supports.

24. The method according to claim 19 wherein the plurality of needle supports are formed out of a radiolucent material, and further wherein radiopaque markers are disposed on the plurality of needle supports.

25. The method according to claim 19 further comprising a spring-loaded syringe assist device for operating the syringe.

26. The method according to claim 19 wherein the syringe comprises (a) a syringe body having a cavity containing the drug and an output port, and (b) a plunger movably disposed in the cavity for driving the drug out of the output port, and further wherein the spring-loaded syringe assist device comprises:
   a housing for mounting to the syringe body;
   a driver for engaging the plunger and moving the plunger so as to drive the drug contained in the cavity out of the output port; and
   a power unit for moving the driver.

27. The method according to claim 26 wherein the power unit comprises a spring.

28. The method according to claim 27 wherein the spring-loaded syringe assist device further comprises a member for releasably holding the spring in an energized condition.

29. The method according to claim 19 wherein the port multiplier comprises:
   a hollow body having an interior;
   an input port in fluid communication with the interior of the hollow body, the input port being configured for attachment to the syringe containing the drug; and
   a plurality of output ports in fluid communication with the interior of the hollow body, each of the plurality of output ports being configured for attachment to a fluid line comprising a needle of the plurality of needles.

30. The method according to claim 29 wherein each of the plurality of output ports comprises a valve for selectively closing off each of the plurality of output ports.

31. A method for delivering a drug, the method comprising:
providing a drug delivery system comprising:
a plurality of needles;
a needle guide for guiding and holding the plurality of needles during insertion into a patient's spine;
a syringe containing the drug which is to be delivered into the patient's spine;
a port multiplier comprising an inlet port connectable to the syringe and a plurality of outlet ports; and
a plurality of tubes for providing fluid connections between the plurality of outlet ports of the port multiplier and the plurality of needles;
wherein the needle guide comprises:
a frame comprising two frame supports connected to one another by at least one adjustable arm, wherein each of the frame supports comprises a frame lumen and a pair of slots communicating with the frame lumen; and
a plurality of needle supports selectively movably mounted to the frame, wherein each of the needle supports is configured to guide and hold a needle of the plurality of needles during insertion into the patient's spine; and
wherein each of the needle supports comprises:
a tubular body slidably disposed in the frame lumen of either frame support, wherein the tubular body comprises a pair of diametrically-opposed openings; and
a tapered member having a first portion smaller than the pair of diametrically-opposed openings and a second portion larger than the pair of diametrically-opposed openings, and a needle lumen extending through the tapered member, the needle lumen being sized to slidably receive and support one of the plurality of needles;
such that (i) the first portion of the tapered member can be disposed in the pair of diametrically-opposed openings, whereby to allow the tubular body to move longitudinally within the frame lumen of either frame support and to rotate relative to a longitudinal axis of either frame support; and (ii) the second portion of the tapered member can be disposed in the pair of diametrically-opposed openings, whereby to lock the tubular body against longitudinal movement and to prevent rotational movement of the tubular body;
positioning the needle guide against the skin of the patient adjacent to the patient's spine;
using the needle guide to guide the plurality of needles as the plurality of needles are inserted into the patient's spine and hold the plurality of needles in position;
connecting the port multiplier to the syringe containing the drug which is to be delivered;
connecting the plurality of tubes to the plurality of outlet ports of the port multiplier and to the plurality of needles; and
using the syringe to eject the drug into the port multiplier, through the plurality of tubes and through the plurality of needles so as to be injected into the desired locations in the patient's spine.

32. The method according to claim 31 wherein each of the needle supports is reconfigurable between (i) a first configuration wherein each needle support is movable axially along the frame and rotatable relative to the frame; and (ii) a second configuration wherein each needle support is axially and rotatably fixed relative to the frame.

33. The method according to claim 32 wherein one needle of the plurality of needles is inserted through one needle support of the plurality of needle supports and into the patient's spine while the one needle support of the plurality of needle supports is in the first configuration, the one needle of the plurality of needles has a disposition checked and corrected as necessary while the one needle support of the plurality of needle supports is in the first configuration, and then the one needle support of the plurality of needle supports is reconfigured into the second configuration while the one needle of the plurality of needles remains inserted into the patient's spine, with the foregoing process thereafter repeated for at least one other of the plurality of needles.

34. The method according to claim 33 wherein the one needle of the plurality of needles has the disposition checked and corrected as necessary using fluoroscopy.

35. The method according to claim 31 wherein the frame supports are formed out of a radiolucent material, and further wherein radiopaque markers are disposed on the frame supports.

36. The method according to claim 31 wherein the plurality of needle supports are formed out of a radiolucent material, and further wherein radiopaque markers are disposed on the plurality of needle supports.

37. The method according to claim 31 further comprising a spring-loaded syringe assist device for operating the syringe.

38. The method according to claim 31 wherein the syringe comprises (a) a syringe body having a cavity containing the drug and an output port, and (b) a plunger movably disposed in the cavity for driving the drug out of the output port, and further wherein the spring-loaded syringe assist device comprises:
a housing for mounting to the syringe body;
a driver for engaging the plunger and moving the plunger so as to drive the drug contained in the cavity out of the output port; and
a power unit for moving the driver.

39. The method according to claim 38 wherein the power unit comprises a spring.

40. The method according to claim 39 wherein the spring-loaded syringe assist device further comprises a member for releasably holding the spring in an energized condition.

41. The method according to claim 31 wherein the port multiplier comprises:
a hollow body having an interior;
an input port in fluid communication with the interior of the hollow body, the input port being configured for attachment to the syringe containing the drug; and
a plurality of output ports in fluid communication with the interior of the hollow body, each of the plurality of output ports being configured for attachment to a fluid line comprising a needle of the plurality of needles.

42. The method according to claim 41 wherein each of the plurality of output ports comprises a valve for selectively closing off each of the plurality of output ports.

* * * * *